United States Patent
Kokubun

(10) Patent No.: US 10,433,803 B2
(45) Date of Patent: Oct. 8, 2019

(54) X-RAY CT APPARATUS AND IMAGE RECONSTRUCTION METHOD

(71) Applicant: HITACHI, LTD., Tokyo (JP)

(72) Inventor: Hiroto Kokubun, Tokyo (JP)

(73) Assignee: HITACHI, LTD., Tokyo (JP)

( * ) Notice: Subject to any disclaimer, the term of this patent is extended or adjusted under 35 U.S.C. 154(b) by 458 days.

(21) Appl. No.: 15/313,707

(22) PCT Filed: Jun. 16, 2015

(86) PCT No.: PCT/JP2015/067293
§ 371 (c)(1),
(2) Date: Nov. 23, 2016

(87) PCT Pub. No.: WO2015/194545
PCT Pub. Date: Dec. 23, 2015

(65) Prior Publication Data
US 2017/0196527 A1    Jul. 13, 2017

(30) Foreign Application Priority Data
Jun. 19, 2014    (JP) .................................. 2014-126257

(51) Int. Cl.
*A61B 6/00*    (2006.01)
*G06T 7/38*    (2017.01)
(Continued)

(52) U.S. Cl.
CPC .......... *A61B 6/5217* (2013.01); *A61B 5/0205* (2013.01); *A61B 6/50* (2013.01);
(Continued)

(58) Field of Classification Search
CPC ......... A61B 5/02; A61B 5/0205; A61B 5/024; A61B 5/02416; A61B 5/02438;
(Continued)

(56) References Cited

U.S. PATENT DOCUMENTS

2007/0030946 A1    2/2007    Tsuyuki et al.
2014/0307935 A1    10/2014   Ishii et al.
2014/0334708 A1    11/2014   Sakata et al.

FOREIGN PATENT DOCUMENTS

JP    6-269445    9/1994
JP    9-75336     3/1997
(Continued)

OTHER PUBLICATIONS

International Search Report in connection with PCT/JP2015/067293.

*Primary Examiner* — Anastasia Midkiff
(74) *Attorney, Agent, or Firm* — Cooper & Dunham LLP

(57) ABSTRACT

An X-ray CT apparatus and an image reconstruction method are configured (i) to determine a movement phase to be used for generating diagnostic images with a small number of operations and (ii) to acquire diagnostic images in a short time while reducing a burden on an operator, such as when the target in scanning is a moving site. For example, an image processing device of an X-ray CT apparatus obtains movement information of a diagnostic site (such as the heart), determines phase selection positions, permits the operator to select an arbitrary movement phase based on the acquired movement information, and reconstructs selection images in a plurality of movement phases for each of the determined phase selection positions using scan data before presentation.

13 Claims, 26 Drawing Sheets

(51) Int. Cl.
  *G06T 7/00* (2017.01)
  *A61B 5/0205* (2006.01)
  *G06T 7/215* (2017.01)
  *H05G 1/62* (2006.01)
  *G06K 9/00* (2006.01)
  *A61B 6/03* (2006.01)
  *A61B 8/08* (2006.01)

(52) U.S. Cl.
  CPC .......... *A61B 6/5288* (2013.01); *G06T 7/0016* (2013.01); *G06T 7/215* (2017.01); *G06T 7/38* (2017.01); *G06T 7/97* (2017.01); *H05G 1/62* (2013.01); *A61B 6/032* (2013.01); *A61B 6/501* (2013.01); *A61B 8/5207* (2013.01); *G06K 2009/00939* (2013.01); *G06T 2207/10081* (2013.01); *G06T 2207/20221* (2013.01); *G06T 2207/30048* (2013.01); *G06T 2211/404* (2013.01)

(58) Field of Classification Search
  CPC .... A61B 6/00; A61B 6/02; A61B 6/03; A61B 6/032; A61B 6/48; A61B 6/486; A61B 6/50; A61B 6/503; A61B 6/504; A61B 6/52; A61B 6/5211; A61B 6/5217; A61B 6/5258; A61B 6/5264; A61B 6/5288; A61B 6/5294; A61B 2576/00; A61B 2576/02; A61B 2576/023; G06T 7/00; G06T 7/0012; G06T 7/0014; G06T 7/0016; G06T 7/174; G06T 7/20; G06T 7/207; G06T 7/215; G06T 7/38; G06T 7/97; G06T 2200/28; G06T 2207/10; G06T 2207/10016; G06T 2207/10072; G06T 2207/10076; G06T 2207/10081; G06T 2207/20; G06T 2207/20021; G06T 2207/30048; G06T 2210/41; G06T 2211/40; G06T 2211/404; G06T 2215/16; H05G 1/60; H05G 1/62; G06K 2009/00939

See application file for complete search history.

(56) References Cited

FOREIGN PATENT DOCUMENTS

| | | |
|---|---|---|
| JP | 2004-187896 | 7/2004 |
| JP | 2007-37782 | 2/2007 |
| JP | 2014-87635 | 5/2014 |
| WO | WO2013/094483 A1 | 6/2013 |

FIG.21

T  SELECTION PRIORITY TABLE

|  | TYPE | SELECTION PRIORITY |
|---|---|---|
| SITE | PROXIMAL | 80 |
| | MEDIAN | 60 |
| | DISTAL | 40 |
| FORM | STENOSIS | 90 |
| | CALCIFICATION | 90 |
| | BRANCHING | 90 |
| ELECTRO-CARDIOGRAPHIC WAVEFORM | NOISE | 30 |
| | ARRHYTHMIA | 50 |
| …… | ….. | …… |

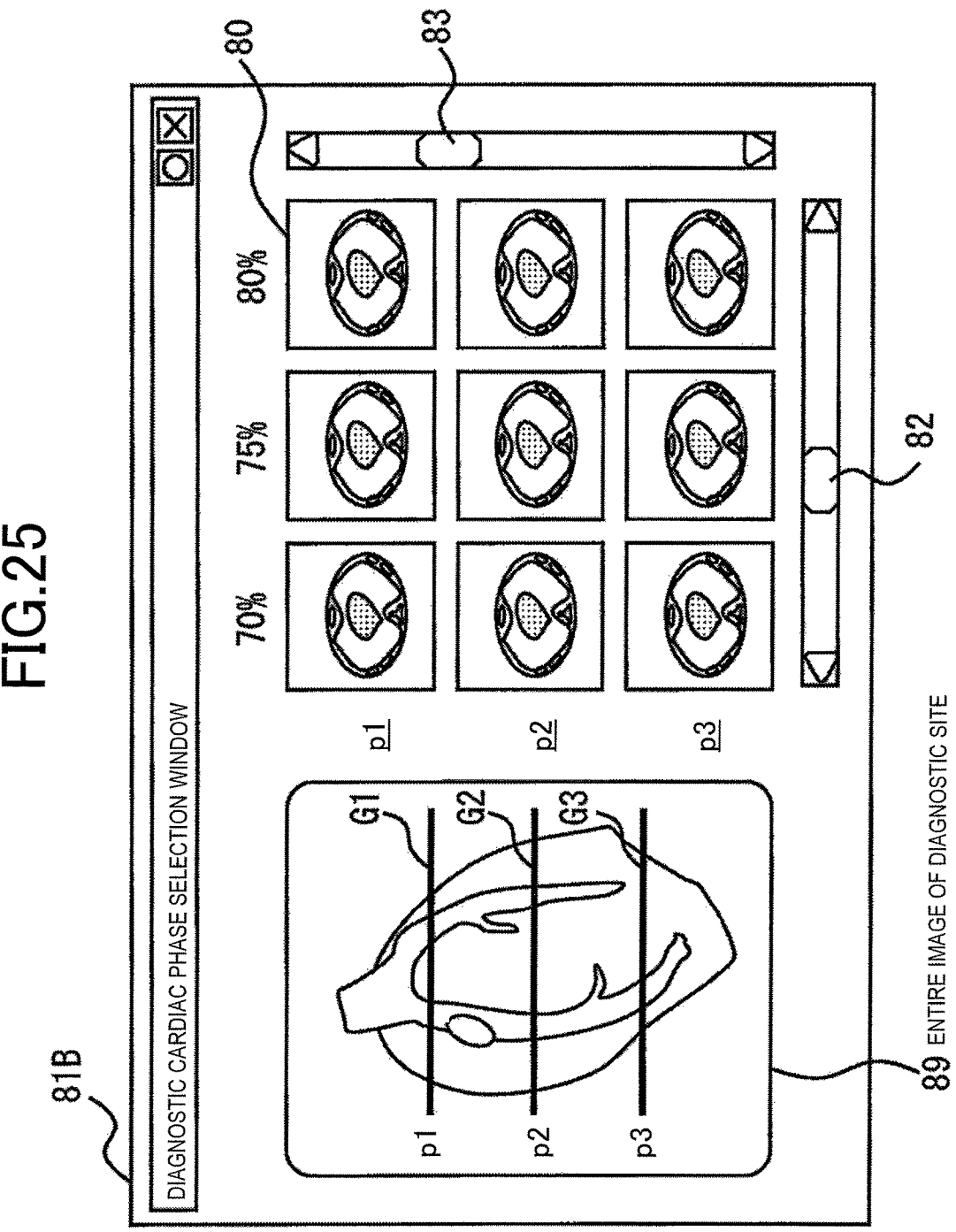

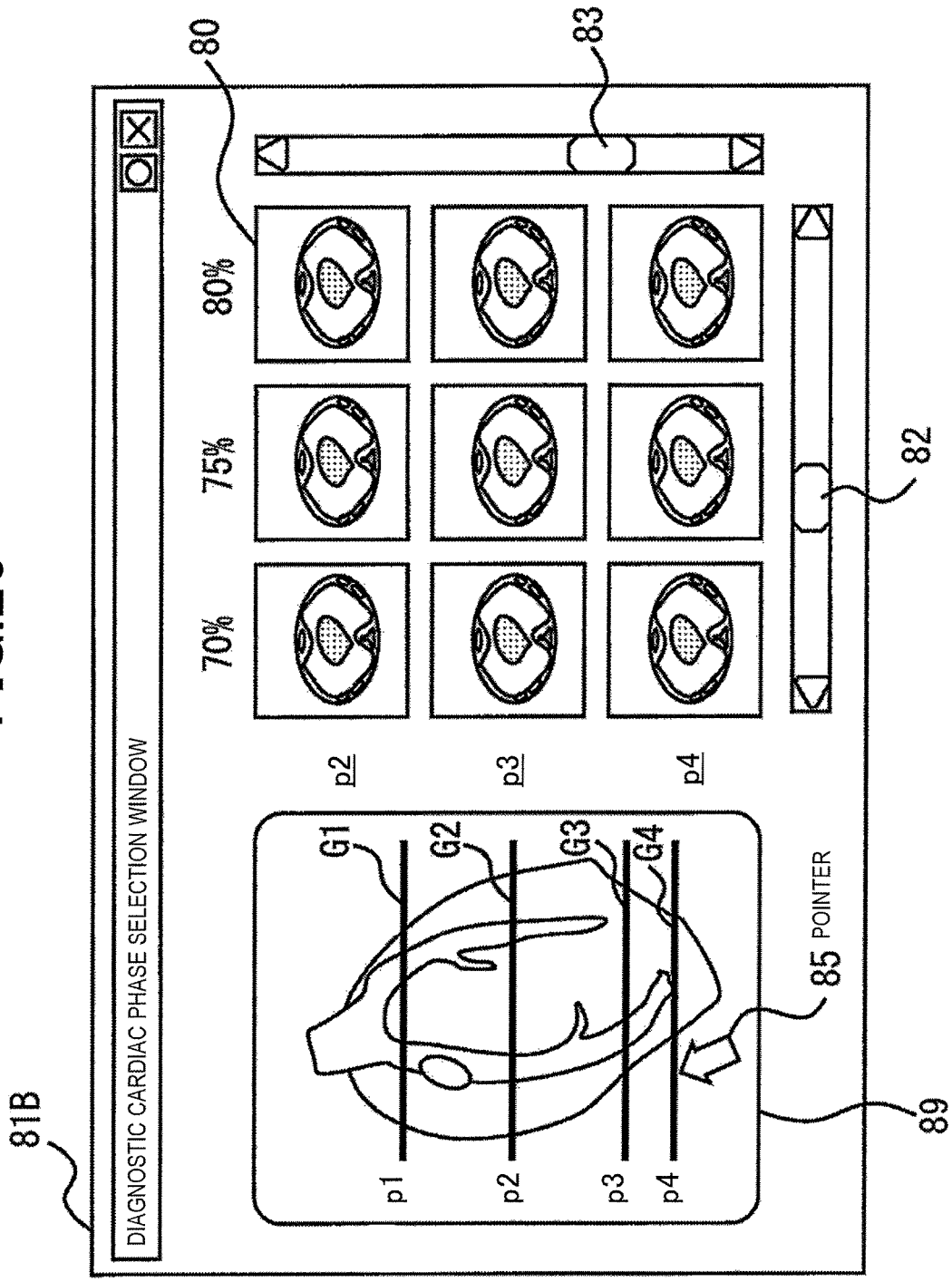

X-RAY CT APPARATUS AND IMAGE RECONSTRUCTION METHOD

TECHNICAL FIELD

The present invention relates to an X-ray CT apparatus and an image reconstruction method and specifically to an operation to select an optimal movement phase for diagnosis of when images of moving sites are reconstructed.

BACKGROUND ART

Conventionally, in a case of scanning a moving site of the body using an X-ray CT (Computed Tomography) apparatus, artifacts caused by the movement are generated on an acquired tomographic image. In order to reduce the artifacts, generally, measurement is additionally performed for physiological movement during scanning using biological sensors such as an electrocardiograph and a respiratory sensor, and scanning is controlled using the acquired measurement signals to generate images.

For example, in a case of scanning the heart as a target, scanning is performed while electrocardiographic information is being measured using an electrocardiograph, and an appropriate cardiac phase is selected later in order to reconstruct a tomographic image in the selected cardiac phase (electrocardiographic synchronous reconstruction method).

As specific examples of the electrocardiographic synchronous reconstruction method, there are a method for performing image reconstruction by determining a scan data range that uses R-waves of an electrocardiographic waveform as a reference and a method for improving time resolution by collecting scan data in which cardiac phases are the same but the scan time is different and combining the collected scan data in order to perform image reconstruction. Although these methods can acquire image data of various cardiac phases using R-waves as a reference, an operator needs to select a diagnostically optimal image from a plurality of image data sets whose phases are different because it is desirable to diagnostically use a tomographic image in which the number of motion artifacts is the least.

On the other hand, there is a method for estimating the cardiac movement in order to automatically generate tomographic images of the heart in an arbitrary cardiac phase, in particular, a phase in which the cardiac movement is the smallest (static cardiac phase) by analyzing scan data or the tomographic images of the heart using the apparatus. For example, according to the method described in PTL 1 (Japanese Patent Publication No. 4157302), the cardiac movement is calculated by analyzing variation amounts of each data from scan data whose scan time is different and a plurality of tomographic images generated from the scan data.

Parameters typically analyzed include an integrated value of a CT value, a distance between feature points, a variation of the center of gravity, etc. Using these methods, an operator does not need to select a cardiac phase to be diagnostically used for an image because the apparatus performs data analysis to evaluate a static cardiac phase.

SUMMARY OF INVENTION

Technical Problem

As shown in the method described in PTL 1, in a case where the apparatus calculates a static cardiac phase, the accuracy is affected by the contents of data to be analyzed and a phase analysis algorithm. Therefore, the static cardiac phase cannot be necessarily evaluated at an accuracy that an operator expects. Also, this causes a problem that it takes a long time to calculate an amount of the analysis.

The present invention was made in light of the above problems, and the purpose is to provide an X-ray CT apparatus and an image reconstruction method that can determine a movement phase to be used for generating diagnostic images with a small number of operations and can accordingly acquire the diagnostic images in a short time while reducing a burden on an operator in scanning in which the target is a moving site.

Solution to Problem

The present invention to achieve the above purpose is an X-ray CT apparatus characterized by comprising: an X-ray source that generates X-rays; an X-ray detector that is placed opposite to the X-ray source and detects X-rays transmitted through an object; a data acquisition device that acquires the transmission X-rays detected by the X-ray detector as scan data; a movement information measuring device that measures movement information of a diagnostic site; a selection image generation unit that obtains the scan data and the movement information of the diagnostic site during scanning, determines phase selection positions in which an operator selects arbitrary movement phases based on the obtained scan data or the acquired movement information, and generates selection images in a plurality of movement phases for each of the determined phase selection positions based on the scan data; and a presentation unit that presents the generated selection images.

Also, an image reconstruction method is characterized by including: a step in which an image processing device obtains scan data and movement information of a diagnostic site during scanning that were measured by the X-ray CT apparatus, determines phase selection positions in which an operator selects arbitrary movement phases based on the obtained scan data or movement information, and generates selection images in a plurality of movement phases for each of the determined phase selection positions based on the scan data; and a step of presenting the generated selection images.

Advantageous Effects of Invention

The present invention can provide an X-ray CT apparatus and an image reconstruction method that can determine a movement phase to be used for generating diagnostic images with a small number of operations and can accordingly acquire the diagnostic images in a short time while reducing a burden on an operator in scanning in which the target is a moving site.

BRIEF DESCRIPTION OF DRAWINGS

FIG. 21 is an example of a selection priority table T.

FIG. 25 is an example of a diagnostic cardiac phase selection window 81B that displays an entire image 89 of a diagnostic site together with the selection images 80.

FIG. 26 is an example of adding a phase selection position by adding a guide display G4 on the entire image 89 in the diagnostic cardiac phase selection window 81B of FIG. 25.

DESCRIPTION OF EMBODIMENTS

Hereinafter, referring to the attached drawings, suitable embodiments of the present invention will be described in detail.

First Embodiment

Figure 1:
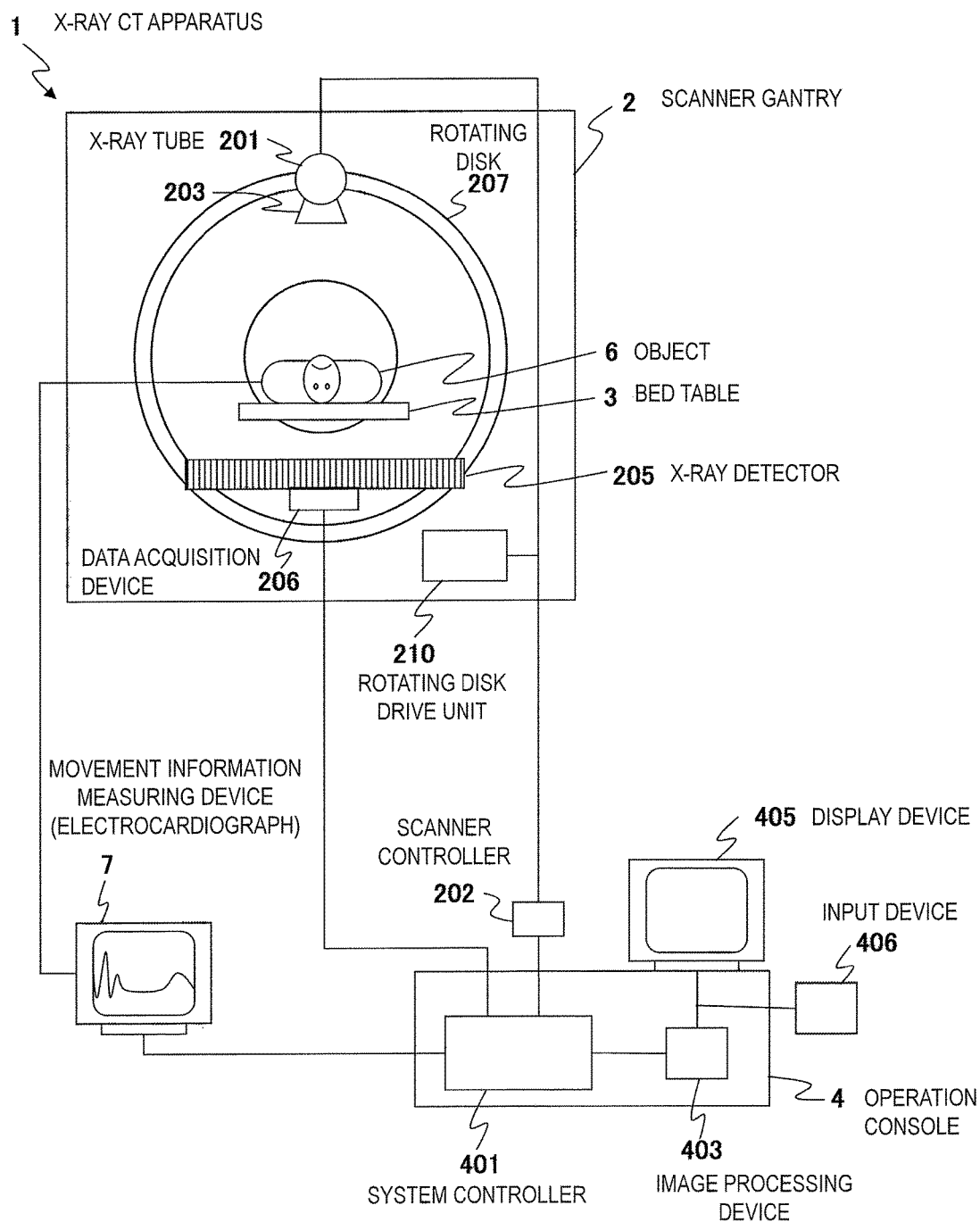
FIG. 1 is an overall configuration diagram of an X-ray CT apparatus 1.

First, referring to FIG. 1, the configuration of the X-ray CT apparatus 1 will be described.

The X-ray CT apparatus 1 is provided with a scanner gantry 2 that irradiates X-rays to an object 6 and detects the X-rays transmitted through the object 6; a bed table 3 that places the object 6; a scanner controller 202 that controls rotary operations and X-ray irradiation operations of the scanner gantry 2; a movement information measuring device (electrocardiograph) 7 that acquires movement information (electrocardiographic information) of the object 6; and an operation console 4 for controlling each part of the X-ray CT apparatus 1. The operation console 4 is provided with a system controller 401, an image processing device 403, a display device 405, and an input device 406.

In the scanner gantry 2, an X-ray tube 201 and a collimator 203 are disposed opposite to an X-ray detector 205 across an opening of a rotary disk 207. The rotary disk 207 is provided with the opening that is an X-ray irradiation space. The bed table 3 placing the object 6 is carried in the opening. The rotary disk 207 is driven so as to rotate around the object 6 by a driving force transmitted through a drive transmission system from a rotating disk drive unit 210.

The X-ray tube 201 is an X-ray source and is controlled by the scanner controller 202 to continuously or intermittently irradiate X-rays of a predetermined strength. The scanner controller 202 controls an X-ray tube voltage and an X-ray tube current that are applied or supplied to the X-ray tube 201 according to the X-ray tube voltage and the X-ray tube current determined by the system controller 401 of the operation console 4. X-rays radiated from the X-ray tube 201 are adjusted by the collimator 203 to be, for example, cone-beam X-rays (cone- or pyramid-shaped beams) irradiated towards the object 6, and an opening width of the collimator 203 is controlled by the scanner controller 202. The X-rays transmitted through the object 6 enter in the X-ray detector 205.

X-ray detection element groups are configured by combination of scintillators and photodiodes (for example, approximately 1,000 elements of the X-ray detection element groups), and approximately 1 to 320 elements of the X-ray detection element groups are arranged in the channel direction (circumference direction) and in the column direction (body-axis direction) in the X-ray detector 205, for example, and the X-ray detector 205 is disposed so as to be opposite to the X-ray tube 201 across the object 6. The X-ray detector 205 detects X-rays radiated from the X-ray tube 201 and transmitted through the object 6 and outputs detected transmission X-ray data to a data acquisition device 206. The data acquisition device 206 collects the transmission X-ray data detected by the respective X-ray detection elements of the X-ray detector 205, converts the data into digital data to output it sequentially to an image processing device 403 of the operation console 4 as scan data.

The scanner controller 202 controls rotations of the X-ray tube 201, the collimator 203, and the rotary disk 207 in the scanner gantry 2 according to control signals transmitted from the system controller 401 of the operation console 4.

A height of the bed table 3 is appropriately adjusted according to a control signal transmitted from the system controller 401 of the operation console 4, and the bed table 3 moves anteroposteriorly in the body-axis direction and moves in a direction (horizontal direction) that is vertical to the body axis and parallel to the bed table 3. Hence, the object 6 is carried in and out of the opening (X-ray irradiation space) of the scanner gantry 2.

The system controller 401 of the operation console 4 is a computer composed of a CPU (Central Processing Unit), a ROM (Read Only Memory), a RAM (Random Access Memory), a storage unit (such as, for example, a hard disk, or another storage device). The system controller 401 controls the scanner gantry 2 (the scanner controller 202), the bed table 3, and the electrocardiograph 7.

The storage unit of the system controller 401 stores images generated by the image processing device 403, and the programs and data, to realize functions of the X-ray CT apparatus 1.

In the system controller 401, transmission X-ray data input from the data acquisition device 206 of the scanner gantry 2 is associated with electrocardiographic information input from the electrocardiograph 7 based on the scan time.

The image processing device 403 performs pre-processes (such as logarithmic transformation, sensitivity correction, etc.) on transmission X-ray data acquired from the data acquisition device 206 in order to generate scan data and reconstructs tomographic images of an object using the scan data. The reconstructed tomographic images are displayed on the display device 405 and are stored in the storage unit of the system controller 401.

Figure 2:
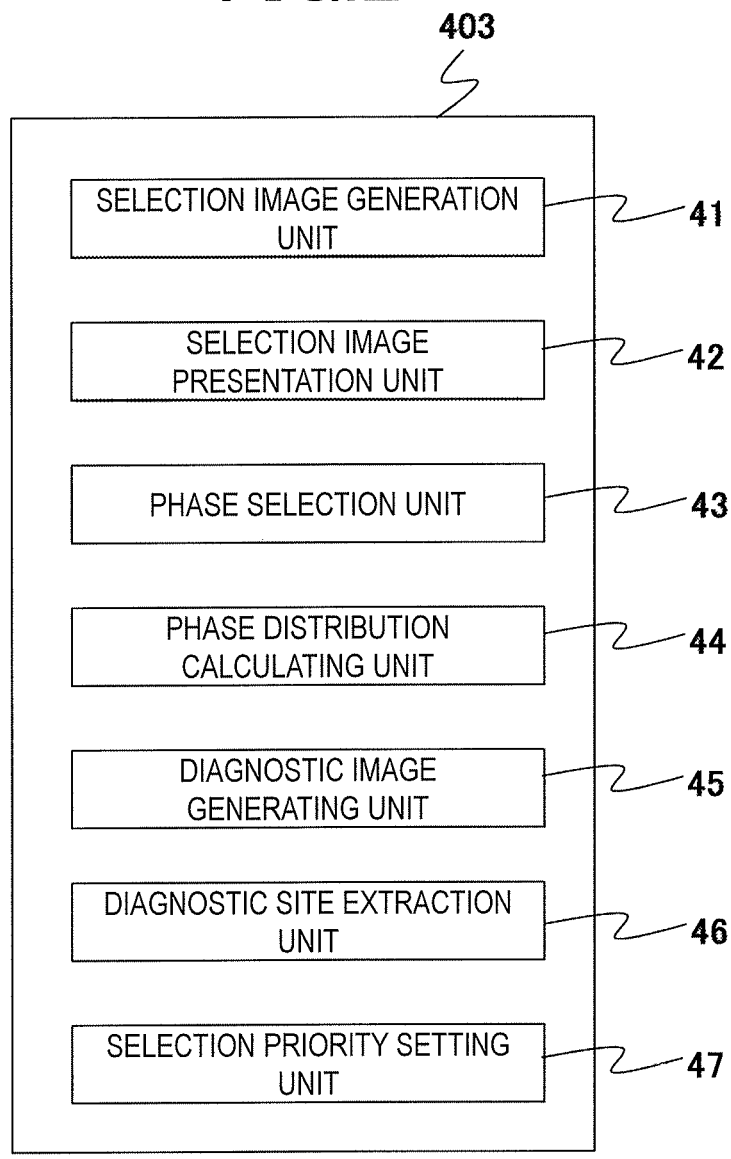
FIG. 2 is a block diagram illustrating a functional configuration of the X-ray CT apparatus 1 related to the present invention.

Also, as illustrated in FIG. 2, the image processing device 403 is configured to include a selection image generation unit 41, a selection image presentation unit 42, a phase selection unit 43, a phase distribution calculating unit 44, a diagnostic image generating unit 45, a diagnostic site extraction unit 46, and a selection priority setting unit 47 so as to realize the functions of the present invention. These parts will be described later.

The display device 405 is composed of a liquid-crystal panel, a display device such as a CRT monitor, and a logic circuit for executing display processes by cooperating with the display device and is connected to the system controller 401. The display device 405 displays reconstruction images output from the image processing device 403 and various information handled by the system controller 401.

The input device 406 is composed of, for example, a pointing device (such as a keyboard and a mouse, a numeric keypad, various switch buttons, etc.) and outputs various commands and information input by an operator to the system controller 401. The operator interactively operates the X-ray CT apparatus 1 using the display device 405 and the input device 406. Additionally, the input device 406 may be a touch panel (or another touch-sensitive means) that is integrally configured with the display screen of the display device 405.

The movement information measuring device (electrocardiograph) 7 measures movement information of a diagnostic site. For example, in a case of scanning the heart region, pulse movement of the heart is measured by the electrocardiograph 7. An electrocardiograph measures electrocardiographic information indicating time variation of an action potential to which the pulse movement of the heart was reflected via an electrode attached to the object 6 and converts the information into digital signals at a predetermined sampling pitch with a 0.1-second interval for example. The electrocardiographic information measured by the electrocardiograph 7 is sequentially transmitted to the system controller 401 and added to projection data by the system controller 401.

Although an electrocardiograph is used as the movement information measuring device 7 because a diagnostic site is set to the heart region as an example in the present embodiment, the present invention can also be applied to diagnostic sites other than the heart region.

For example, in a case of setting a diagnostic site to the lung region, a respirometer (or a similar device) that measures respiratory movement may be used as the movement information measuring device 7.

Next, referring to FIG. 2, a functional configuration of the X-ray CT apparatus 1 will be described.

In a case of reconstructing an image of a moving diagnostic site such as the heart (or another site), it is desirable that the image processing device 403 generates tomographic images in an optimal movement phase (for example, a phase with less movement).

However, the pulsations of the heart are not strictly the same in the same phase of the entire heart. That is, the entire heart is not in a static state in the same cardiac phase. Also, it is very troublesome for an operator to manually determine a cardiac phase for each of slice positions of the entire heart. Therefore, the X-ray CT apparatus 1 of the present invention is provided with the functions shown in FIG. 2 in order to generate tomographic images (diagnostic images) in the processing procedure shown in FIG. 3.

As shown in FIG. 2, the X-ray CT apparatus 1 includes the selection image generation unit 41, the selection image presentation unit 42 (a presentation unit), the phase selection unit 43, the phase distribution calculating unit 44 (a calculating unit), the diagnostic image generating unit 45 (an image reconstruction unit), the diagnostic site extraction unit 46 (an extraction unit), and the selection priority setting unit 47 (a setting unit) as a functional configuration to realize the present invention. Although the respective functional units are provided in the image processing device 403 in FIG. 2, the respective functional units may be provided in the system controller 401.

The selection image generation unit 41 obtains transmission X-ray data (scan data) detected by the scanner gantry 2 and movement information (electrocardiographic information measured by the electrocardiograph 7) of a diagnostic site during scanning, determines a phase selection position that is a body-axis direction position in which an operator selects an arbitrary movement phase based on the acquired movement information, and generates the selection images 80 (FIG. 7) in a plurality of movement phases for each of the determined phase selection positions based on the scan data. The phase selection position is provided by setting a period in the movement information as a reference. Alternatively, a site presenting anatomical features or a diagnostically important site may be set as the phase selection position (a second embodiment).

The selection image presentation unit 42 transmits the selection images 80 in a plurality of movement phases that were generated by the selection image generation unit 41 to the display device 405 and displays the images so that an operator can inspect them. Referring to the displayed selection images 80, the operator determines and selects an optimal movement phase in each of the phase selection positions.

The phase selection unit 43 receives selection of an arbitrary movement phase from the selection images 80 in the plurality of movement phases that were presented by the selection image presentation unit 42. The phase selection unit 43 notifies the phase distribution calculating unit 44 of the movement phase selected and input by the operator through the input device 406.

The phase distribution calculating unit 44 calculates the movement phase distribution 90 of the entire diagnostic site based on a movement phase in each of the phase selection positions selected by the phase selection unit 43. The movement phase distribution 90 (FIG. 9) shows a distribution of an optimal movement phase (diagnostic phase) in each body-axis direction position of the diagnostic position. The movement phase distribution 90 is employed to determine the diagnostic phase in each body-axis direction position other than the phase selection positions. The movement phase distribution 90 is evaluated using the above phase selection positions and the movement phase selected in each phase selection position as indexes. For example, the movement phase distribution 90 may be a curve or a straight line evaluated by interpolation calculation based on a relationship between the phase selection positions and the movement phases selected in each phase selection position or may be an average value of movement phases selected in a plurality of phase selection positions, or another collection of values.

The diagnostic image generating unit 45 determines movement phases (diagnostic phases) reconstructing the respective diagnostic images IMG_z1, IMG_z2, IMG_z3, . . . for the respective body-axis direction positions z1, z2, z3, . . . based on the above movement phase distribution 90 and reconstructs tomographic images (diagnostic images IMG_z1, IMG_z2, IMG_z3, . . . ) in the determined movement phases for the respective body-axis direction positions.

In a case of setting a site presenting anatomical features or a diagnostically important site as the phase selection position, the diagnostic site extraction unit 46 is further provided in addition to the above functional configuration (a third embodiment). The diagnostic site extraction unit 46 generates evaluation images 50 (FIG. 14) of a diagnostic site based on scan data and extracts a site presenting anatomical features or a diagnostically important site of the diagnostic site from the evaluation images 50. The selection image generation unit 41 sets body-axis direction positions including the site presenting anatomical features or the diagnostically important site that were extracted by the diagnostic site extraction unit 46 as phase selection positions. The details of this process will be described in the third embodiment.

The selection priority setting unit 47 in a case where the selection image presentation unit 42 presents the selection images 80 in an order from a phase selection position with higher priority (an eighth embodiment). The selection priority setting unit 47 receives settings of selection priority of phase selection positions and stores the priority settings in the storage unit of the system controller 401. The selection priority may be previously input by an operator or may be previously stored in the storage unit. The details of this process will be described in the eighth embodiment.

Next, referring to FIG. 3, operations of the X-ray CT apparatus 1 will be described.

Figure 3:
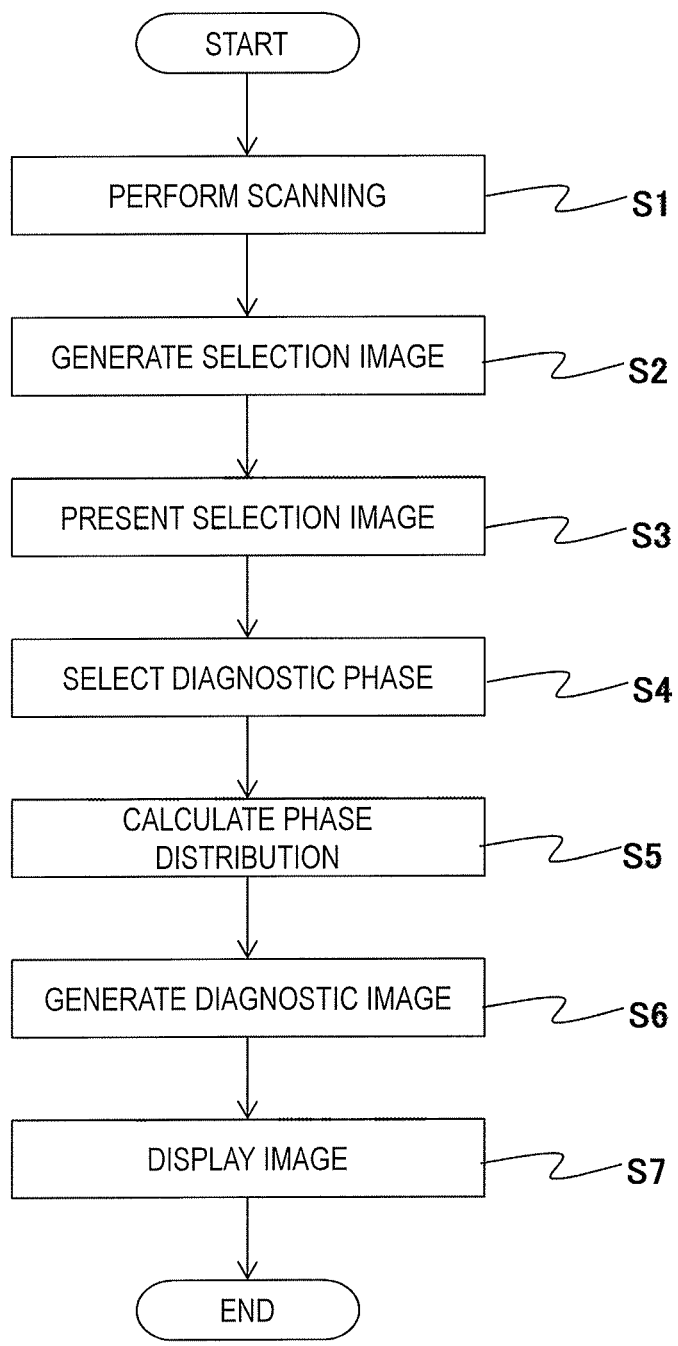
FIG. 3 is a flow chart illustrating an overall process flow to be executed by the X-ray CT apparatus 1.

The X-ray CT apparatus 1 of the present embodiment executes an image reconstruction process using the procedure in the flow chart of FIG. 3. That is, a CPU of the system controller 401 reads out programs and data related to the image reconstruction process illustrated in FIG. 3 from the storage unit and executes processes based on the programs and the data.

First, the X-ray CT apparatus 1 performs scanning on a moving site according to operations of an operator. In the following description, scanning is performed on the heart as a target. Cardiac movement of an object (electrocardiographic information) is also acquired simultaneously during scanning using the electrocardiograph 7 (Step S1). The system controller 401 transmits scan data acquired from the scanner gantry 2 and the electrocardiographic information acquired from the electrocardiograph 7 to the image processing device 403.

The image processing device 403 generates the selection images 80 to be used by an operator to select a diagnostic phase (Step S2). In Step S2, the image processing device 403 determines phase selection positions based on the movement information acquired in Step S1 and generates the selection images 80 in a plurality of movement phases for each of the determined phase selection positions.

The phase selection positions are body-axis direction positions where an operator selects a diagnostic phase. For example, in a case where periodic movement is found in the movement information acquired in Step S1, it is considered that the phase selection positions are determined using the period as a reference.

Hereinafter, described will be an example of generating images of the heart. In order to generate tomographic images in an arbitrary movement phase (cardiac phase), the image processing device 403 performs an electrocardiographic synchronous reconstruction method. Although the electrocardiographic synchronous reconstruction method includes various methods, some tomographic images whose cardiac phases are different are generally first generated using an R-wave position of an electrocardiographic waveform as a reference to set the tomographic images as the selection images 80.

Figure 4:
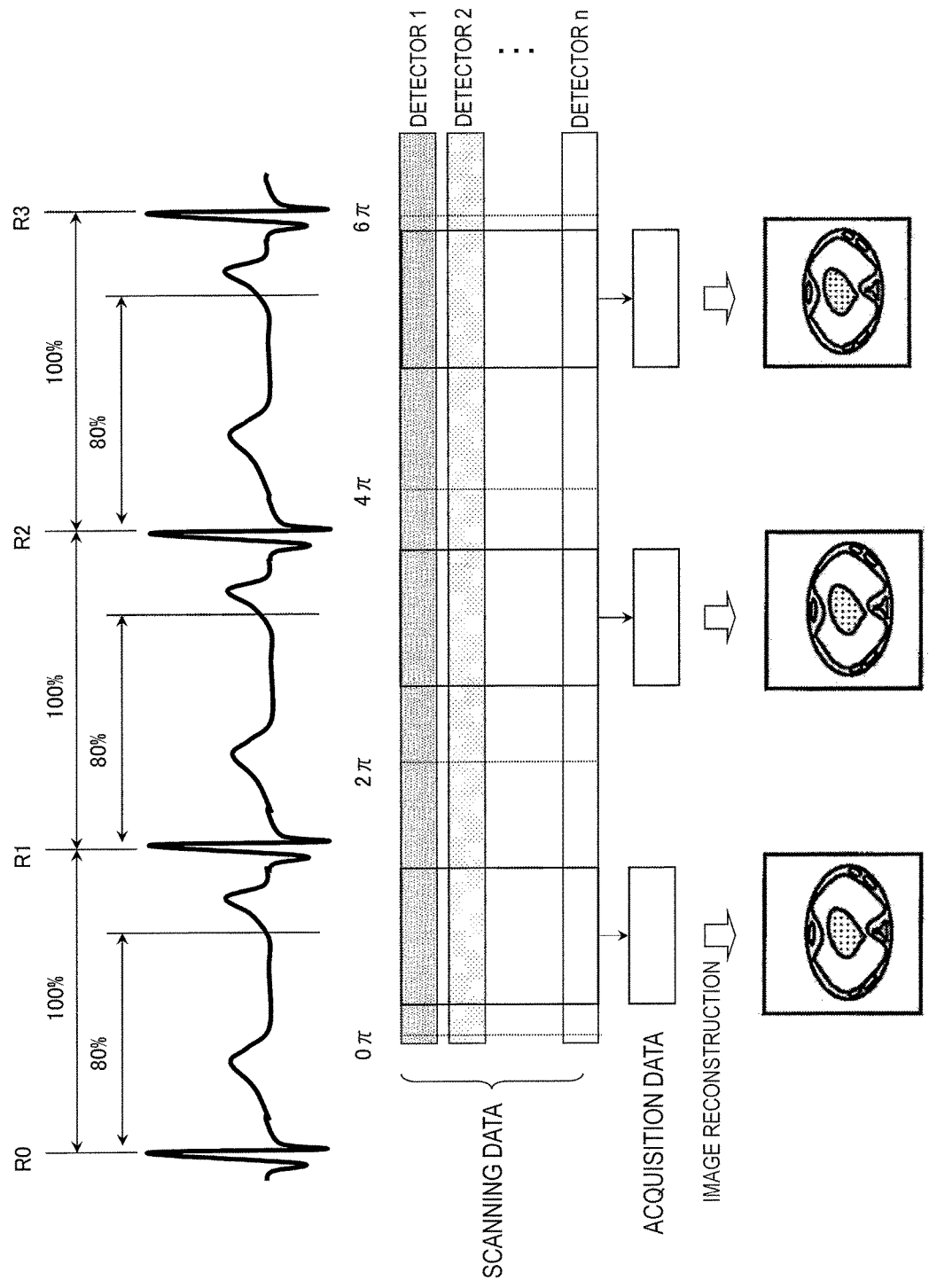
FIG. 4 illustrates an example of an electrocardiographic synchronous reconstruction method.

FIG. 4 illustrates an example of generating tomographic images in cardiac phases whose relative positions of adjacent R-waves (peaks of an electrocardiographic waveform) are 80% (such positions being also referred to herein as "80% positions", and such phases being also referred to herein as "at time of the 80% positions"). The waveform of FIG. 4 indicates the electrocardiographic waveform acquired by the electrocardiograph 7. As illustrated in FIG. 4, data scanned at time of the 80% positions using the R-waves as references is extracted by the number of scanning angles (approximately 180 degrees) required for reconstruction in order to perform image reconstruction. Also, in order to generate tomographic images in an arbitrary body-axis direction position, a data set in the same slice position is generated by performing an interpolation process between scan data acquired from each detector row before the image reconstruction. It is noted that scan data whose cardiac phases are different in the same scanning position is acquired by performing scanning at a low speed in a case of using the electrocardiographic synchronous reconstruction method.

As described above, because ranges of scan data that are extracted are different depending on an R-wave that is employed as a reference in the electrocardiographic synchronous reconstruction, the R-wave employed during reconstruction considerably affects a feature of tomographic images that are generated based on the data.

Figure 5:
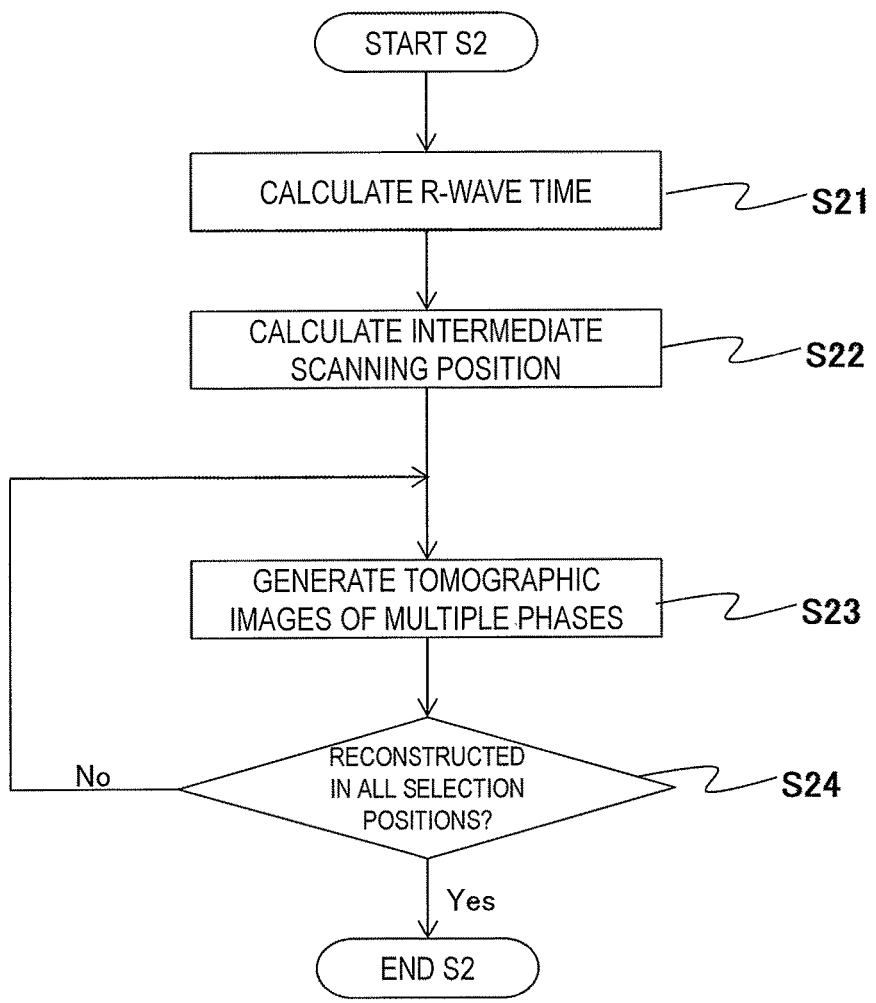
FIG. 5 is a flow chart illustrating an example of a processing procedure of a selection image generation process in Step S2 of FIG. 3.

FIG. 5 illustrates a process flow of determining phase selection positions using a period in movement information as a reference in order to generate the selection images 80.

First, the image processing device 403 evaluates time when R-waves are recorded from the electrocardiographic information acquired in Step S1 (Step S21). Next, the image processing device 403 calculates scanning positions (body-axis direction positions) at the intermediate time between adjacent R-waves and sets the calculated scanning positions as image reconstruction positions (hereinafter, referred to as phase selection positions) of the selection images 80 (Step S22). The intermediate time may be an exactly intermediate time between two adjacent R-wave times or may be a time corresponding to the other preset phase. That is, phase selection positions are respectively determined for each pulse using an R-wave shown periodically as a reference.

The image processing device 403 respectively generates tomographic images (the selection images 80) of a plurality of phases in the respective phase selection positions calculated in Step S22 (Step S23). The tomographic images of a plurality of phases mean tomographic images whose body-axis direction positions (phase selection positions) are the same and whose cardiac phases are different. It is desirable that the cardiac phases in which the selection images 80 are generated are phases around a static phase. For example, a plurality of tomographic images whose cardiac phases are different are generated between 75% and 95%. Also, phase intervals of the selection images 80 that are generated are previously set at appropriate intervals such as 5% intervals and 1% intervals.

The image processing device 403 determines whether or not the selection images 80 has been reconstructed in all the phase selection positions (Step S24) and repeatedly executes the process of Step S23 (tomographic image generation) until the reconstruction in all the phase selection positions ends (Step S24: No→Step S23). When the reconstruction of the tomographic images (the selection images 80) of a plurality of movement phases ends in all the phase selection positions (Step S24: Yes), the Step S2 processes (selection image generation processes) end and shift to Step S3 of FIG. 3.

In the selection image presentation process in Step S3 of FIG. 3, tomographic images (the selection images 80) of a plurality of phases in each of the phase selection positions that were generated in Step S2 are arranged and displayed on the display device 405 (Step S3). An operator refers to a plurality of the displayed selection images 80 and selects a cardiac phase appropriate for diagnosis in each of the phase selection positions (Step S4).

Figure 6:
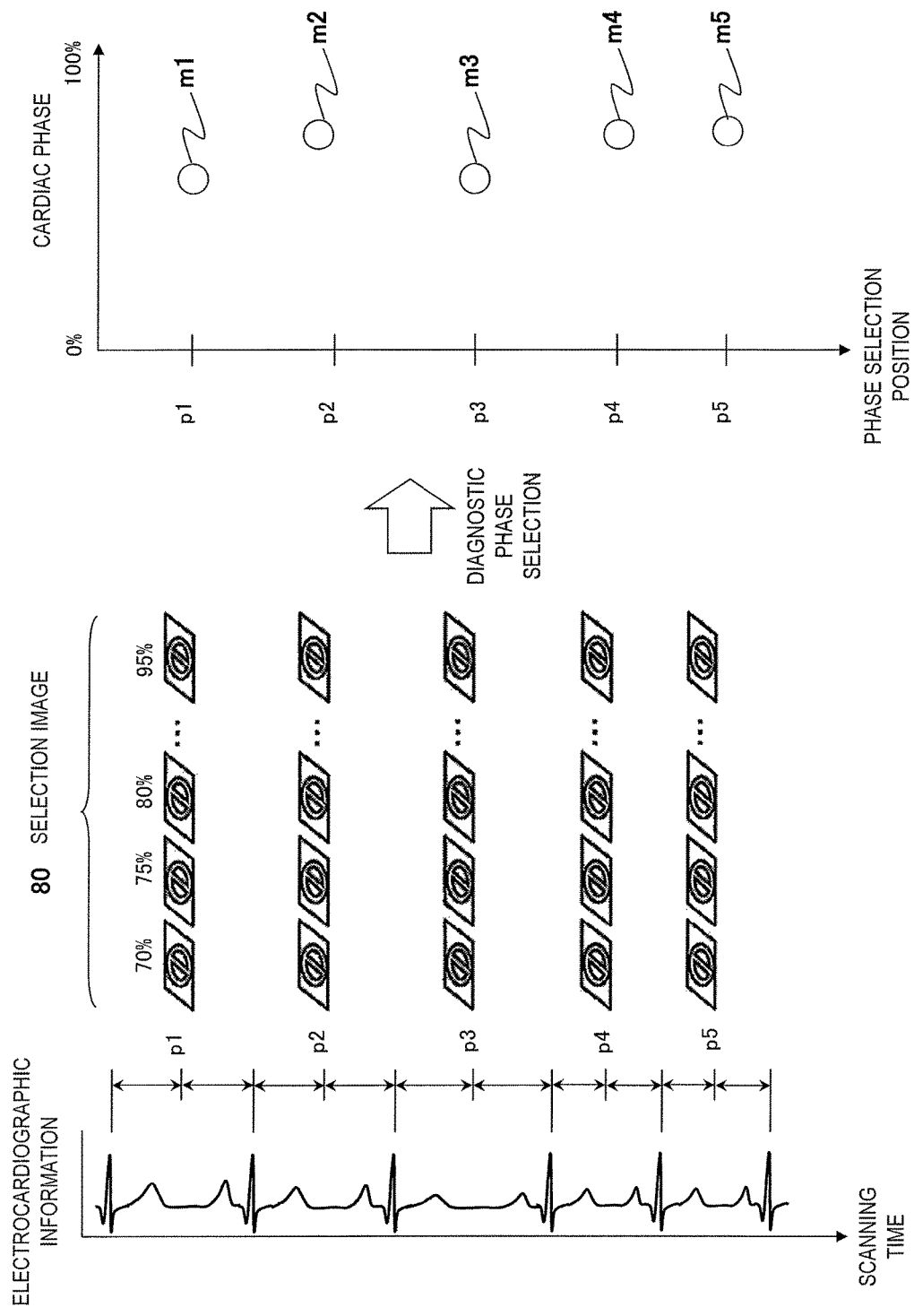
FIG. 6 illustrates Step S2 (selection image generation process) to Step S4 (diagnostic phase selection process) of FIG. 3.

FIG. 6 illustrates a series of processes from Step S2 to Step S4.

The left diagram of FIG. 6 shows an electrocardiographic waveform, and the vertical axis and the horizontal axis are a time axis and electrocardiographic information respectively. The image processing device 403 recognizes R-wave positions from the electrocardiographic waveform acquired during scanning and calculates scanning positions p1, p2, p3, p4, and p5 at the intermediate time between adjacent R-waves in order to set phase selection positions. Then, the respective tomographic images in cardiac phases between 70% and 95% are reconstructed, for example, at 5% intervals in the respective phase selection positions p1, p2, p3, p4, and p5. The image processing device 403 arranges and displays the generated tomographic images (the selection images 80) on the display device 405.

Figure 7:
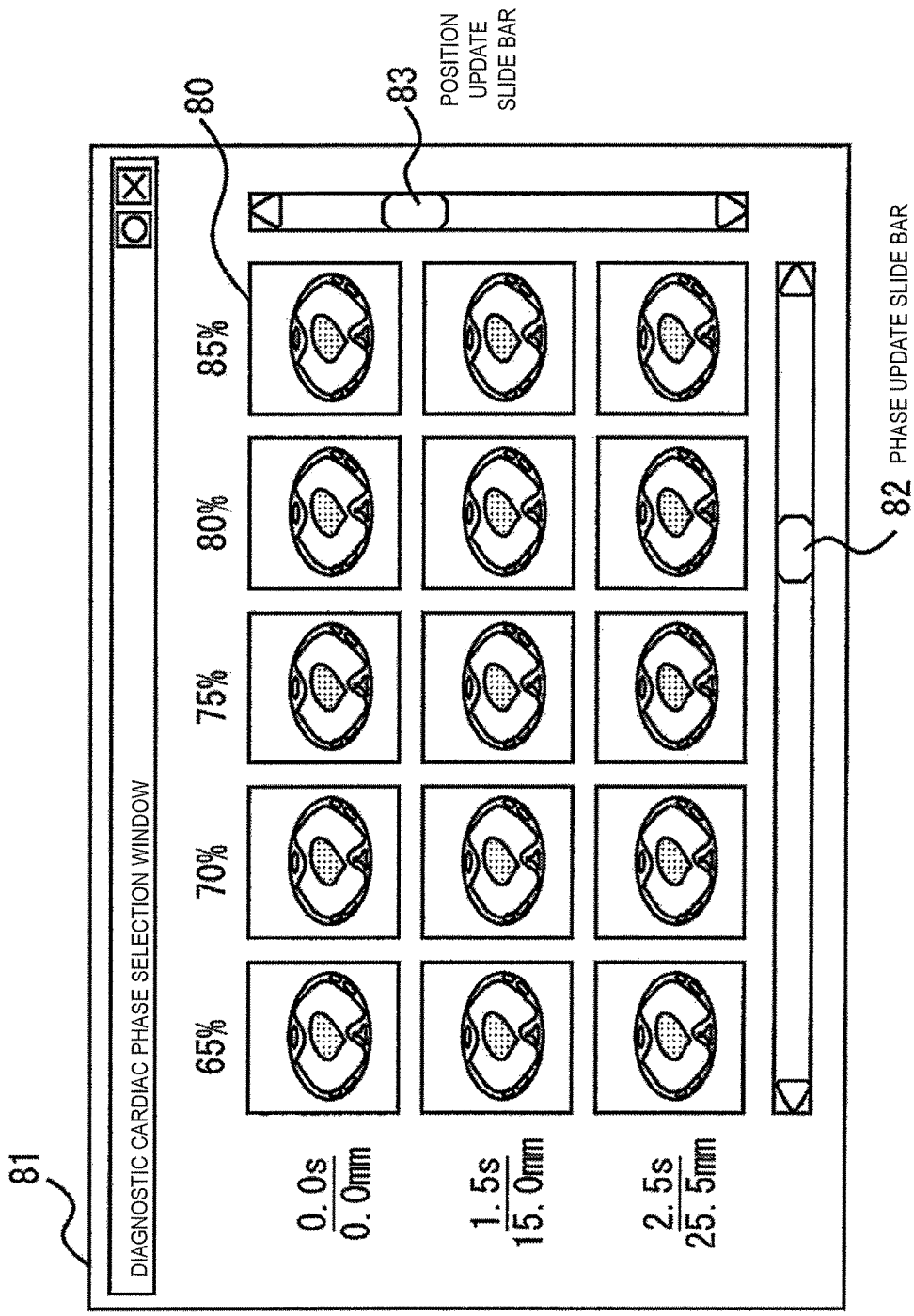
FIG. 7 is an example of a diagnostic cardiac phase selection window 81 presenting a plurality of selection images 80.

FIG. 7 illustrates an example of the phase selection window 81 that is an example of a GUI (Graphical User Interface) in which the selection images 80 are arranged and selectably displayed. In the diagnostic cardiac phase selection window (phase selection window) 81 of FIG. 7, the horizontal direction shows cardiac phases, the vertical direction shows phase selection positions, and the selection images 80 corresponding to the vertical and horizontal positions are displayed in a grid pattern. In a case where all the selection images 80 cannot be displayed on one window due to limitation of the display window size, a position update slide bar 83 and a phase update slide bar 82 are desirably disposed in the vicinity of the selection image group so that the selection images 80 displayed in the window can be updated.

An operator operates a pointer 85 (refer to FIG. 8) on the window using the input device 406 such as a mouse and clicks each of the selection images 80 in order to select a diagnostic cardiac phase for each of the phase selection positions.

Figure 8:
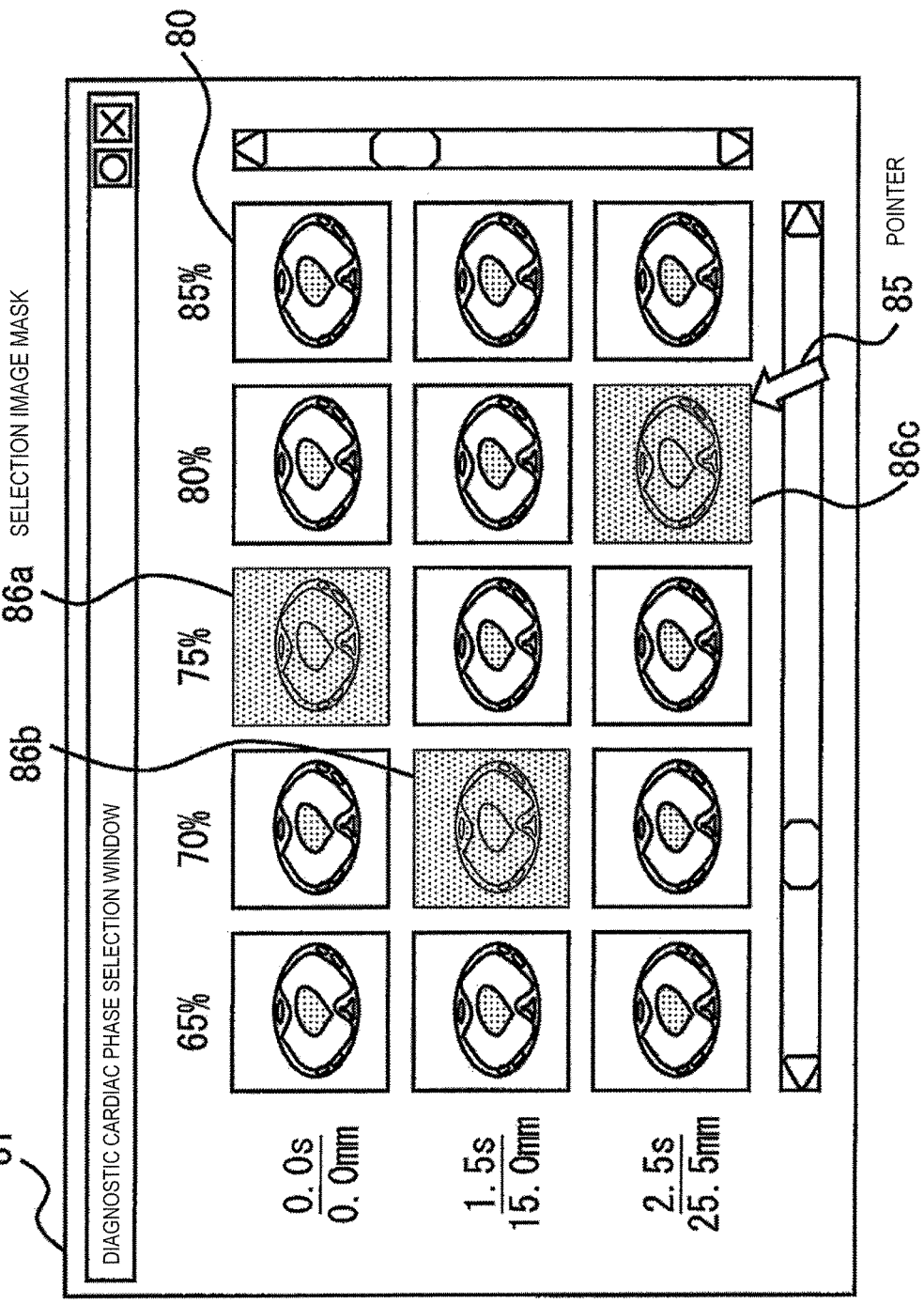
FIG. 8 is a diagram illustrating a state where some of the selection images 80 are selected in the diagnostic cardiac phase selection window 81 of FIG. 7.

FIG. 8 illustrates a state where the cardiac phase "75%" for the phase selection position "0.0 mm"; the cardiac phase "70%" for the phase selection position "15.0 mm"; and the cardiac phase "80%" for the phase selection position "25.5 mm" are selected in the phase selection window 81. It is desirable that the unselected selection images 80 are displayed in a discriminable manner by covering the selected selection images 80 with selection image masks 86a, 86b, and 86c, reverse-displaying the selected selection images 80, or displaying the selected selection images 80 in a manner that is different than that in which the unselected images are displayed.

Thus, after a diagnostic phase is selected in each phase selection position by an operator, the image processing device 403 next calculates the movement phase distribution 90 of the entire diagnostic site based on the movement phase in each phase selection position selected by the operator (Step S5). Then, the image processing device 403 generates tomographic images for diagnosis (diagnostic images) according to the movement phase distribution 90 calculated in Step S5 (Step S6).

Referring to the right diagram of FIG. 6 and FIG. 9, the processes of Steps S5 and S6 will be described.

In the diagnostic phase selection process of Step S4, movement phases (hereinafter, referred to as diagnostic phases) m1 to m5 that generate diagnostic images in each of phase selection positions p1 to p5 are selected as shown in the right diagram of FIG. 6. The selected diagnostic phases m1 to m5 are not necessarily equal in each of the phase selection positions p1 to p5. Additionally, the phase selection positions p1 to p5 are discontinuous in the body-axis direction. Therefore, the image processing device 403 calculates the movement phase distribution 90 indicating optimal diagnostic phases in each of body-axis direction positions of the entire diagnostic site based on the phase selection positions p1 to p5 and the diagnostic phases m1 to m5 selected in each of the phase selection positions p1 to p5 (refer to the left diagram of FIG. 9).

Figure 10:
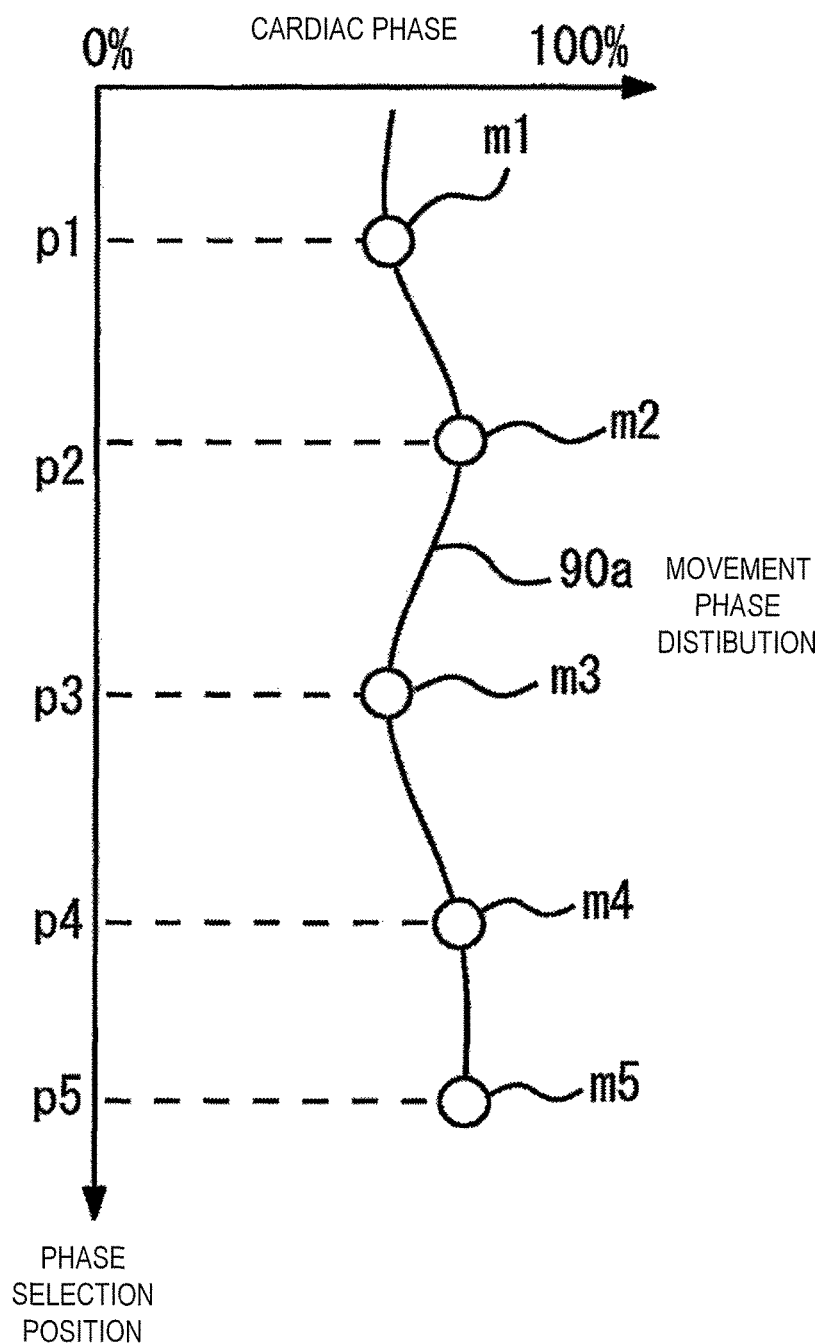
FIG. 10 is an example of a movement phase distribution 90a calculated by spline interpolation.

In order to calculate the movement phase distribution 90, a polynomial expression is used for representing a smooth curve passing through each of the movement phases m1 to m5 selected using a distance between a movement phase and a phase selection position that are adjacent and selected as an index, and the polynomial expression is used as the movement phase distribution 90 as illustrated in FIG. 10 for example. Such a polynomial expression may, for example, be used in a mathematical method to represent a spline curve or another line or collection of continuous points.

Figure 11:
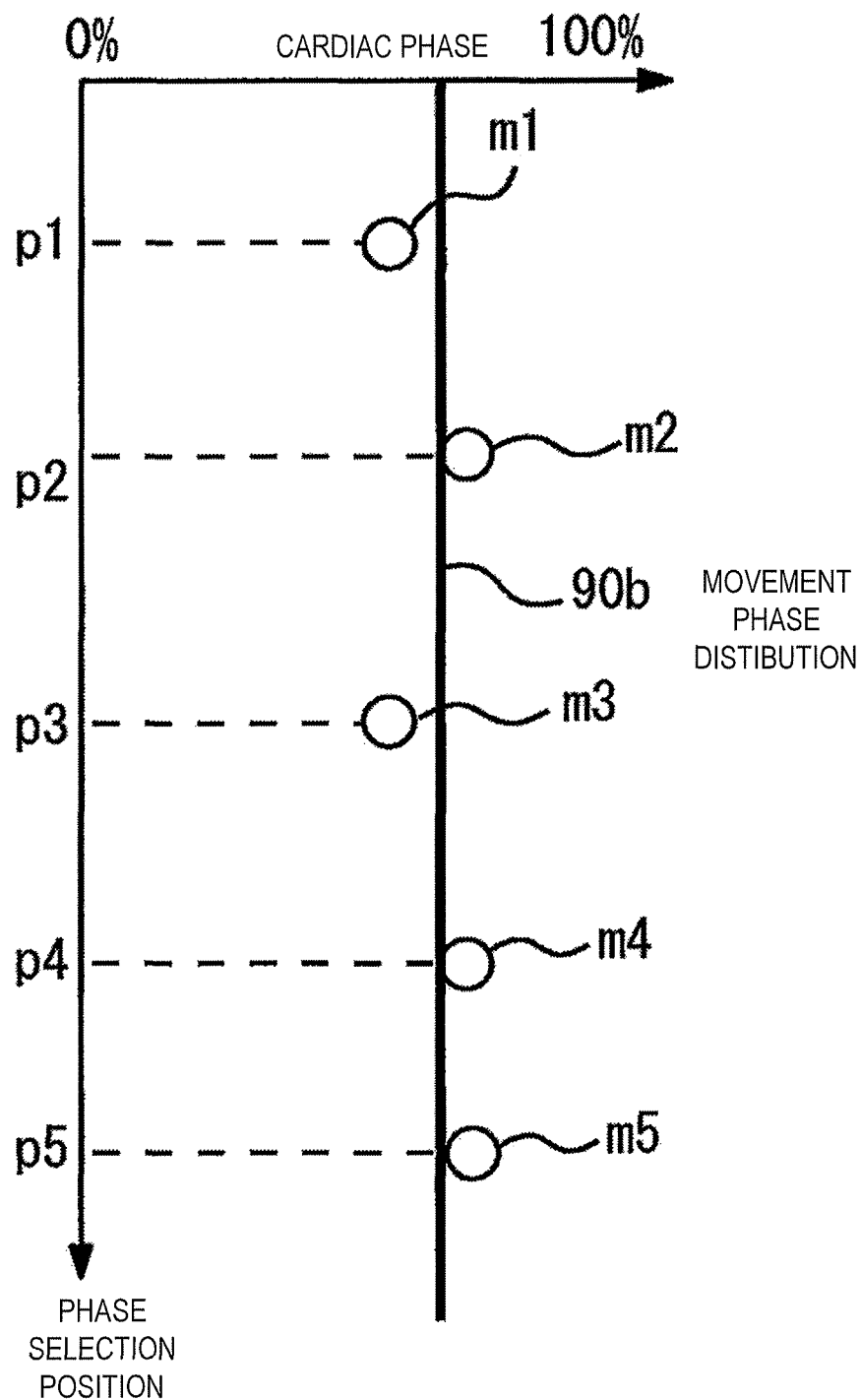
FIG. 11 is an example of a movement phase distribution 90b calculated by an average value.

Also, as illustrated in FIG. 11, the movement phase distribution 90 may be an average value of movement phases m1 to m5 selected in a plurality of phase selection positions p1 to p5.

It is noted that methods for calculating the movement phase distributions 90 (90a and 90b) are not limited to the above examples.

Any methods including an interpolation method that obtains a curve or a straight line connecting a plurality of points smoothly may be used.

Thus, when the image processing device 403 calculates the movement phase distributions 90, diagnostic phases can be determined in each of body-axis direction positions $z1$, $z2$, ... other than phase selection positions $p1$ to $p5$ based on the movement phase distributions 90.

Figure 9:
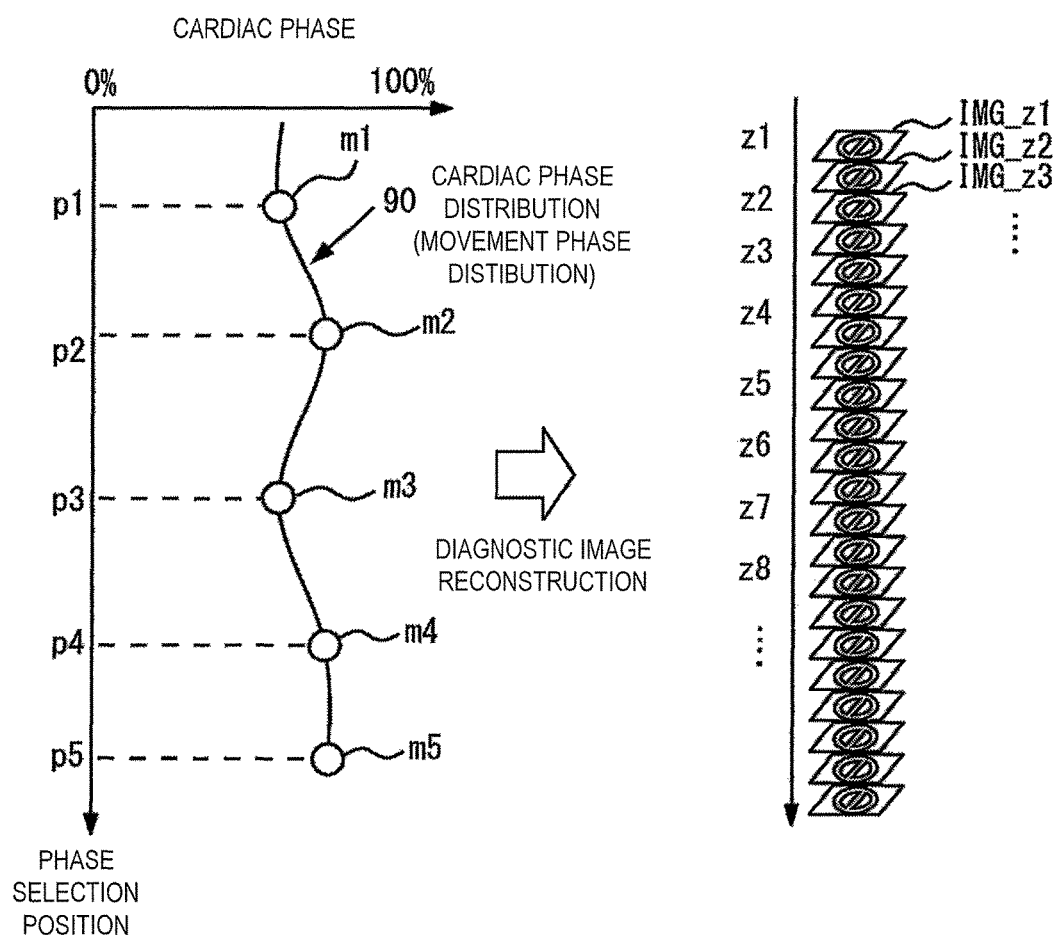
FIG. 9 illustrates Step S5 (calculation process of a movement phase distribution 90) to Step S6 (diagnostic image generation process) of FIG. 3.

The image processing device 403 reconstructs diagnostic tomographic images (diagnostic images) IMG_z1, IMG_z2, ... respectively for each of body-axis direction positions $z1$, $z2$, ... based on the movement phase distributions 90 as illustrated in FIG. 9. The diagnostic tomographic images are tomographic images reconstructed under reconstruction conditions suitable for diagnosis. The image processing device 403 displays the generated diagnostic tomographic images IMG_z1, IMG_z2, ... on the display device 405 (step S7). Hence, an operator can perform diagnosis by referring to the diagnostic tomographic images IMG_z1, IMG_z2, ...

As described above, the X-ray CT apparatus 1 of the first embodiment measures movement information of a diagnostic site during scanning, determines phase selection positions $p1$, $p2$, ... so that an operator selects an arbitrary movement phase based on the measured movement information, and then generates and presents the selection images 80 in a plurality of movement phases for each of the determined phase selection positions $p1$, $p2$, ... using scan data. Hence, a plurality of the selection images 80 can be presented not for all the body-axis direction positions but for some phase selection positions, which can significantly reduce the number of the selection images 80 that are generated.

Also, the X-ray CT apparatus 1 receives selection of an arbitrary movement phase from the presented selection images 80, calculates the movement phase distributions 90 in the body-axis direction of the entire diagnostic site based on the movement phase selected by an operator, determines diagnostic phases respectively for each of body-axis direction positions $z1$, $z2$, according to the calculated movement phase distributions 90, and then reconstructs diagnostic images IMG_z1, IMG_z2, ... of the respective body-axis direction positions in the determined diagnostic phases. This can generate the diagnostic images IMG_z1, IMG_z2, ... of each slice by automatically calculating an optimal movement phase in a position that the operator did not select. Therefore, the optimal movement phase can be determined with a small number of operations for each slice, and the diagnostic images can be generated in the optimal movement phase in each body-axis direction position.

Although cardiac phases are described using relative positions (%) between adjacent R-waves as references, the description may be made using an absolute time from a single R-wave as a reference.

Also, although a case where a diagnostic site is the heart is described as an example, an application target of the present invention is not limited to the heart but can be applied to scanning of all the moving sites.

Second Embodiment

Next, a second embodiment of the present invention will be described.

It is noted that the same parts as the first embodiment are denoted by the same reference signs in the following descriptions, and the repeated descriptions will be omitted.

In the first embodiment, described is an example in which intermediate positions between adjacent R-waves are set as phase selection positions in a case where the number of reference R-waves is one (one-period pulse) for reconstructing tomographic images. In a case of performing an electrocardiographic synchronous reconstruction method of a more complex algorithm, there is a case where appropriate phase selection positions cannot be acquired using the process flow of FIG. 5. For example, in order to improve time resolution, used is a method referred to as an electrocardiographic synchronous segment reconstruction method that combines scan data of a plurality of pulses to generate a tomographic image. In this case, multiple periods of reference R-waves are used for generating one tomographic image.

Figure 12:
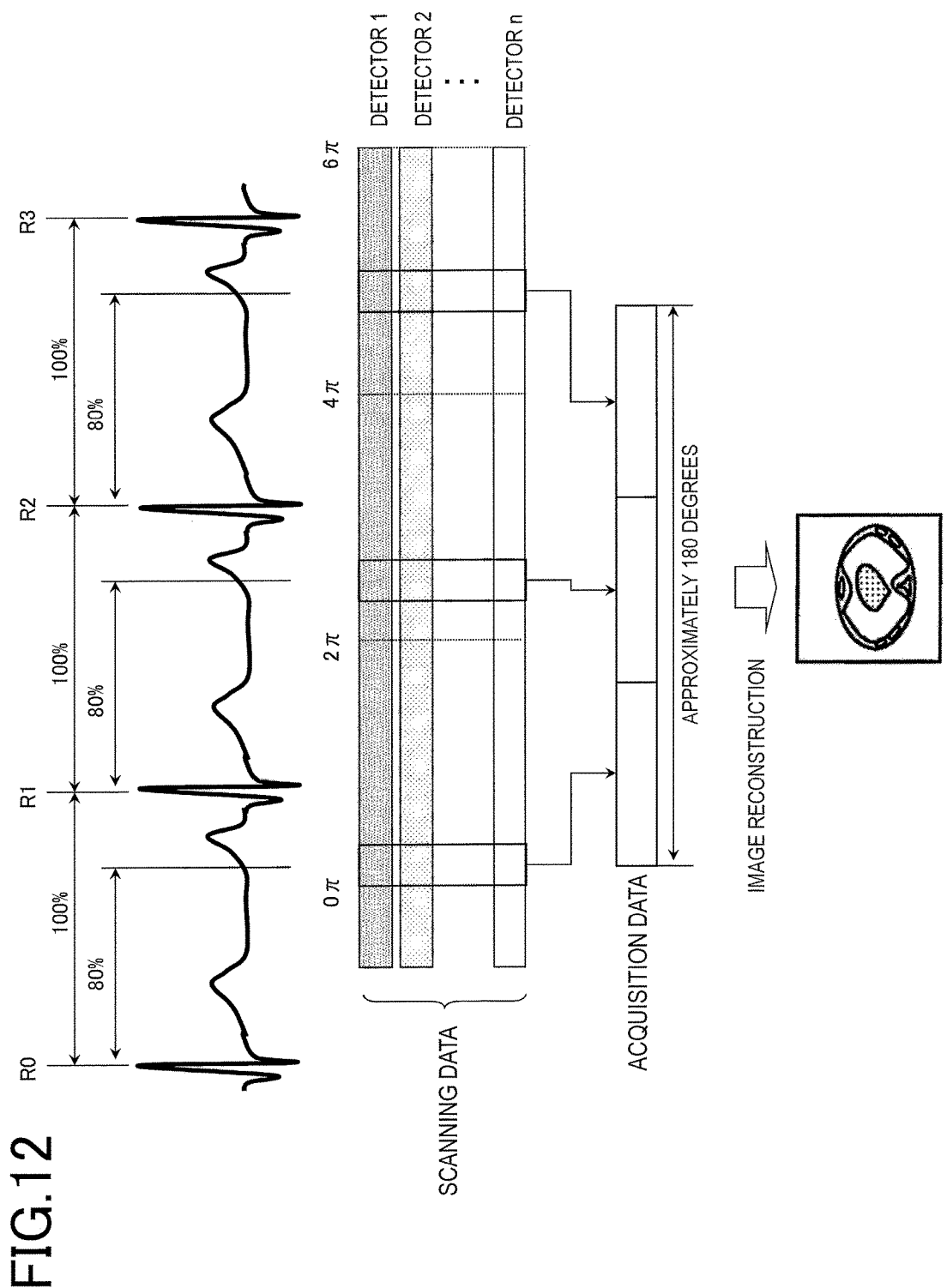
FIG. 12 illustrates the electrocardiographic synchronous reconstruction method (electrocardiographic synchronous segment reconstruction method).

FIG. 12 illustrates the electrocardiographic synchronous segment reconstruction method. FIG. 12 shows a case of generating a tomographic image in relative positions 80% of adjacent R-waves. As illustrated in FIG. 12, in the electrocardiographic synchronous segment reconstruction method, the image processing device 403 collects divided scan data whose scanning angles are different in the same phase from scan data acquired in three pulses for example by the number of scanning angles (approximately 180 degrees) required for reconstruction.

Specifically, divided scan data is collected, in which extraction ranges are 0 to $\frac{1}{3}\pi$ from scan data between R0 and R1; $\frac{1}{3}\pi$ to $\frac{2}{3}\pi$ from scan data between R1 and R2; and $\frac{2}{3}\pi$ to $\pi$ from scan data between R2 and R3, in the example of FIG. 12. Then, image reconstruction is performed using scan data of approximately 180 degrees acquired by combining these divided scan data. Also, in order to generate a tomographic image in an arbitrary body-axis direction position, a data set in the same slice position is generated by performing an interpolation process between scan data acquired from each detector row before the image reconstruction. In a case of using an image reconstruction method in which scan data of a plurality of pulses is combined, it is desirable that phase selection positions are determined in the processing procedure illustrated in FIG. 13 in order to generate the selection images 80.

Figure 13:
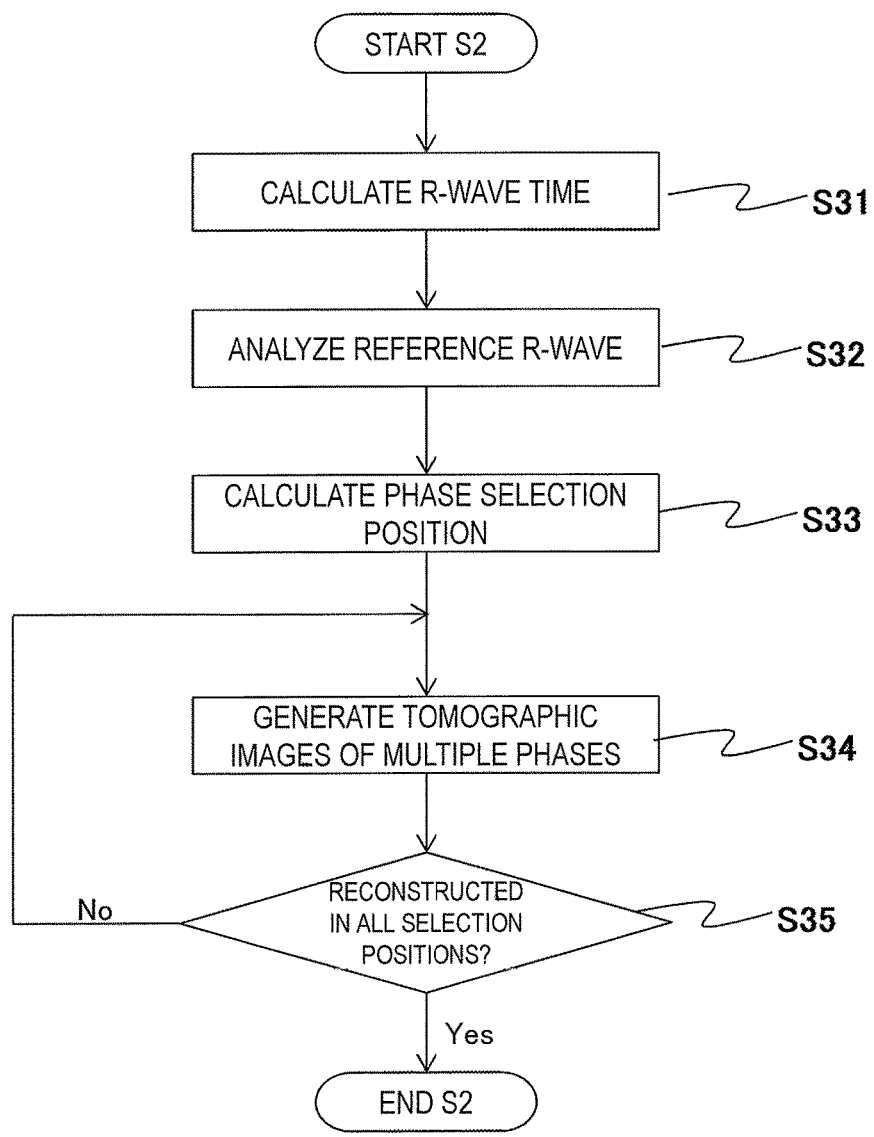
FIG. 13 is a flow chart illustrating a processing procedure of the selection image generation process (Step S2 of FIG. 3) in a case of using the electrocardiographic synchronous segment reconstruction method.

FIG. 13 illustrates a process flow of a suitable selection image generation process (Step S2 of FIG. 3) in a case of using scan data of a plurality of pulses in order to generate tomographic images.

First, the image processing device 403 evaluates time when an R-wave is recorded from electrocardiographic information acquired in Step S1 of FIG. 3 (Step S31). Next, the image processing device 403 analyzes an R-wave that is employed in order to reconstruct tomographic images in scanning positions and cardiac phases in an arbitrary range (which pulse the scan data to be used belongs to) (Step S32). In a case of performing an electrocardiographic synchronous segment reconstruction method illustrated in FIG. 12, because a plurality of pulses are employed for each image of one scanning position and one cardiac phase, the image processing device 403 evaluates a plurality of reference R-wave groups for each scanning position and each cardiac phase and records them in a RAM.

There is no need to actually perform the electrocardiographic synchronous segment reconstruction method in Step S32, and information of the reference R-waves is simply calculated.

The image processing device 403 uses a scanning position at which the contents of the reference R-wave analyzed in Step S32 switches as a reference in order to determine phase selection positions (Step S33). For example, in a case where the reference R-waves transition by a group unit for each scanning position such as cases where a reference R-wave combination is (R1, R2, R3) in scanning positions $z1$ to $z3$, where a reference R-wave combination is (R2, R3, R4) in scanning positions z4 to z6, where a reference R-wave combination is (R3, R4, R5) in scanning positions z7 to z9, . . . , a position at which the contents of the reference R-waves change is used as a reference in order to set the scanning positions z3, z6, and z9 as the phase selection positions.

The image processing device 403 generates tomographic images (the selection images 80) in a plurality of phases respectively for each of the phase selection positions calculated in Step S33 (Step S34) and repeatedly executes the Step S34 process (tomographic image generation) until reconstruction ends in all the phase selection positions (Step S35: No→Step S34). When the reconstruction ends in all the phase selection positions (Step S35: No), the Step S2 process (selection image generation process) of FIG. 3 ends, and the procedure shifts to Step. S3.

As described above, in the second embodiment, reference R-waves during image reconstruction can be used as a reference in order to determine phase selection positions. Hence, the suitable selection images 80 can be generated and presented even in a case of using an electrocardiographic synchronous segment reconstruction method a more complex algorithm to reconstruct one image by combining scan data of multiple periods.

Third Embodiment

Next, a third embodiment of the present invention will be described.

Although phase selection positions are determined based on a period of a movement phase in the first and second embodiments, the third embodiment is not limited to this. The phase selection positions may be a site presenting anatomical features of the diagnostic site or a diagnostically important site.

Figure 14:
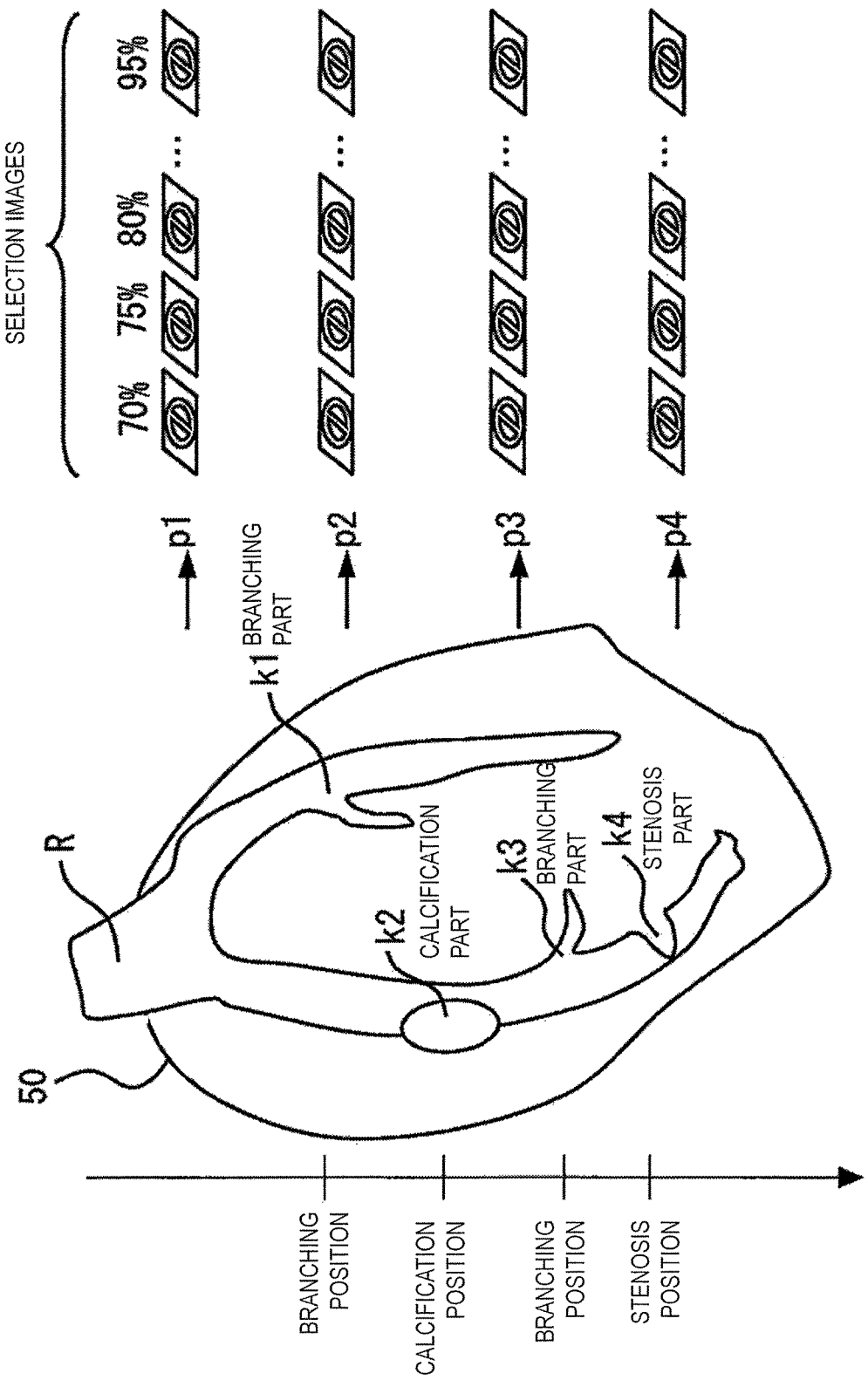
FIG. 14 illustrates an example in which a phase selection position is set as a body-axis direction position including a feature part of a diagnostic site and a diagnostically important site.

The left diagram of FIG. 14 is an evaluation image 50 that illustrates the entire heart. In a case of scanning the heart as a target, a site presenting anatomical features of the diagnostic site or a diagnostically important site is, for example, one or more parts, such as branching parts k1 and k3 of coronary arteries, a stenosis part k4 of a coronary artery, a calcification k2 around the coronary artery, etc. In the third embodiment, the image processing device 403 is provided with the diagnostic site extraction unit 46 that extracts the site presenting anatomical features of the diagnostic site or the diagnostically important site and uses body-axis direction positions including sites extracted by the diagnostic site extraction unit 46 as phase selection positions p1 to p4 in order to generate the selection images 80.

Figure 15:
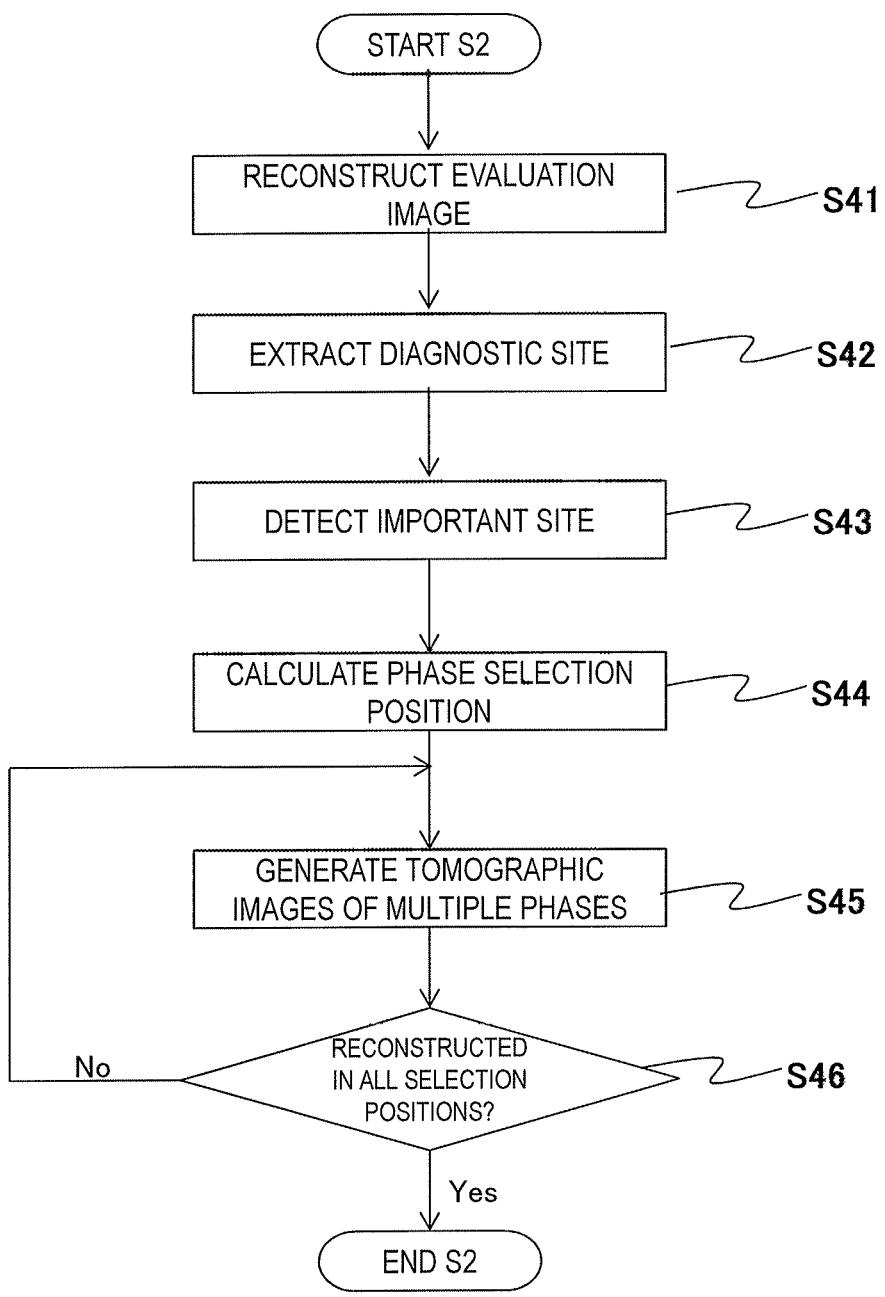
FIG. 15 is a flow chart illustrating a procedure of the selection image generation process (Step S2 of FIG. 3) in a case of setting the phase selection position as the body-axis direction position including a feature part of a diagnostic site and a diagnostically important site.

FIG. 15 is a flow chart illustrating a processing procedure for determining phase selection positions using an importance of a site to be diagnosed as a reference.

First, the image processing device 403 generates an evaluation image of a diagnostic site based on scan data obtained by scanning in Step S1 of FIG. 3 (Step S41). Because the evaluation image is used for analyzing an important site, it is desirable to perform image reconstruction in a cardiac phase estimated to have as less motion artifacts as possible. The evaluation image may be generated using a publicly-known electrocardiographic synchronous segment reconstruction method (such as the method illustrated in FIGS. 4 and 12). Next, the image processing device 403 extracts a diagnostic site from the evaluation image generated in Step S41 (Step S42). For example, in FIG. 14, a coronary artery R is extracted. The extraction process of the diagnostic site may be performed using a publicly-known method. For example, a detection algorithm of three dimensional directions such as a region growing method is used as a general method for extracting a desired region from the image.

Next, the image processing device 403 detects a diagnostically important site from the diagnostic site (coronary artery R) extracted in Step 42 (Step S43). A method for detecting the important site varies depending on a target to be detected. For example, in order to detect the branching parts k1 and k3 of coronary arteries, a publicly know algorithm in which a blood vessel core line is calculated to detect a core line branching part may be used. Also, in order to detect the stenosis part k4 of the coronary artery R, a diameter of the extracted coronary artery is measured, and diameter variation in a blood vessel running direction is checked. Also, for detecting a lesion part such as the calcification k2, known is a method for detecting a position where a lesion exists by analyzing a distribution of pixel values (CT values) around the blood vessel.

When a diagnostically important site is detected in Step S43, the image processing device 403 calculates the phase selection positions p1 to p4 based on positional information of the detected important site (Step S44). In the example of FIG. 14, the phase selection positions p1 and p3 are body-axis direction positions corresponding to the branching parts k1 and k3 of the coronary artery R, the phase selection position p2 is a body-axis direction position corresponding to the calcification part k2, and the phase selection position p4 is a body-axis direction position corresponding to the stenosis part k4.

When the phase selection positions p1 to p4 are determined, the image processing device 403 generates tomographic images of a plurality of phases (the selection images 80) respectively in the determined phase selection positions p1 to p4 (Step S45). Until the selection images 80 are reconstructed in all the phase selection positions p1 to p4, the Step S45 process will be repeatedly executed (Step S46: No→Step S45). When the selection images 80 are reconstructed in all the phase selection positions p1 to p4 (Step S46: Yes), the Step S2 process (selection image generation process) of FIG. 3 ends, and then the procedure shifts to Step S3 of FIG. 3.

As described above, the image processing device 403 generates evaluation images based on scan data, extracts a diagnostically important site and a site presenting anatomical features by analyzing the evaluation images, and sets body-axis direction positions including the extracted sites as phase selection positions. Hence, the selection images 80 of various movement phases can be generated in the phase selection positions to which attention is paid during diagnosis.

Fourth Embodiment

Next, a fourth embodiment of the present invention will be described. Although detection time of reference R-waves is used as a reference to calculated phase selection positions in the process flows of FIGS. 5 and 13 (the first and second embodiments), scanning positions where movement information could not be normally acquired may be used as a reference to determine the phase selection positions.

Figure 16:
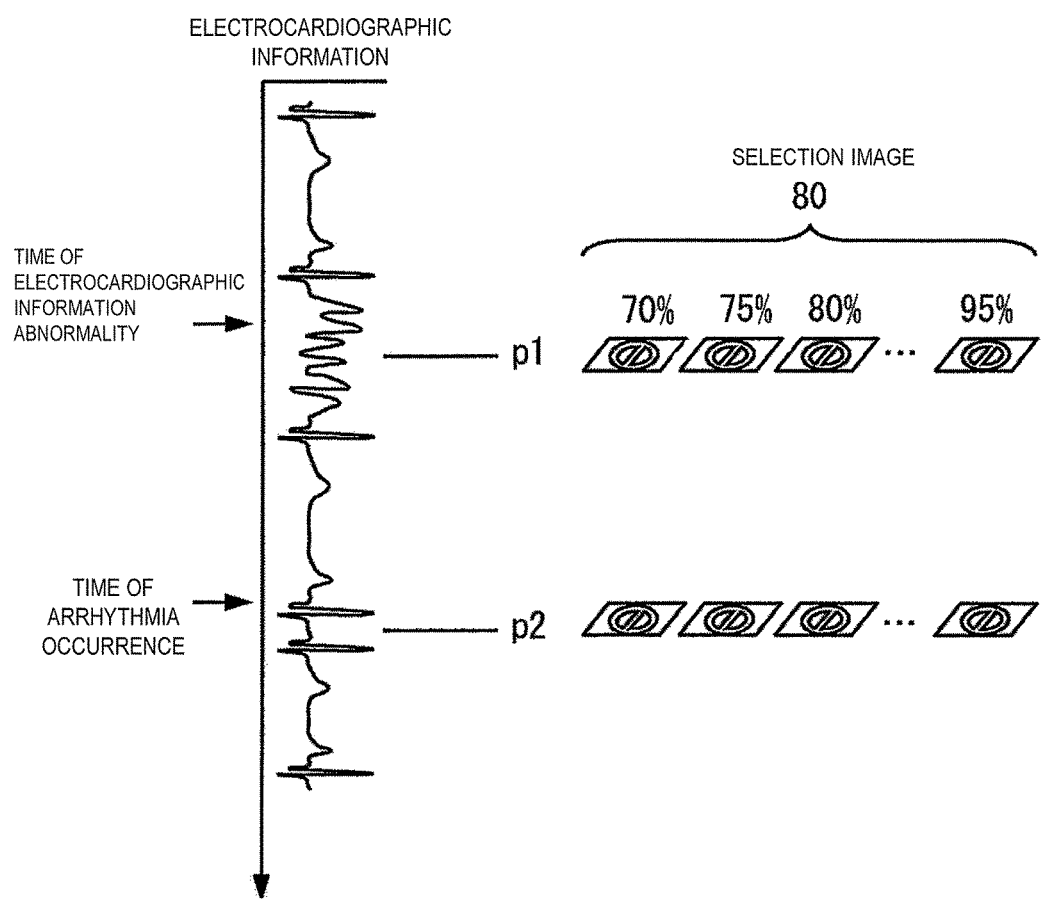
FIG. 16 illustrates an example in which a phase selection position is set as a body-axis direction position scanned at a time when movement information has an abnormality.

FIG. 16 illustrates a process of using an abnormal state of movement information as a reference to determine phase selection positions.

Abnormalities in electrocardiographic information that can be assumed include noise mixed due to failure of the electrocardiograph 7, physical abnormalities such as arrhythmia, and/or other abnormalities. In such a state where the abnormalities are included in the electrocardiographic information, there is a case where expected electrocardiographic synchronous reconstruction is not performed. Therefore, by setting these abnormality occurrence positions as phase selection positions, an operator can pay much attention in such a phase selection positions to select a movement phase suitable for diagnosis.

Figure 17:
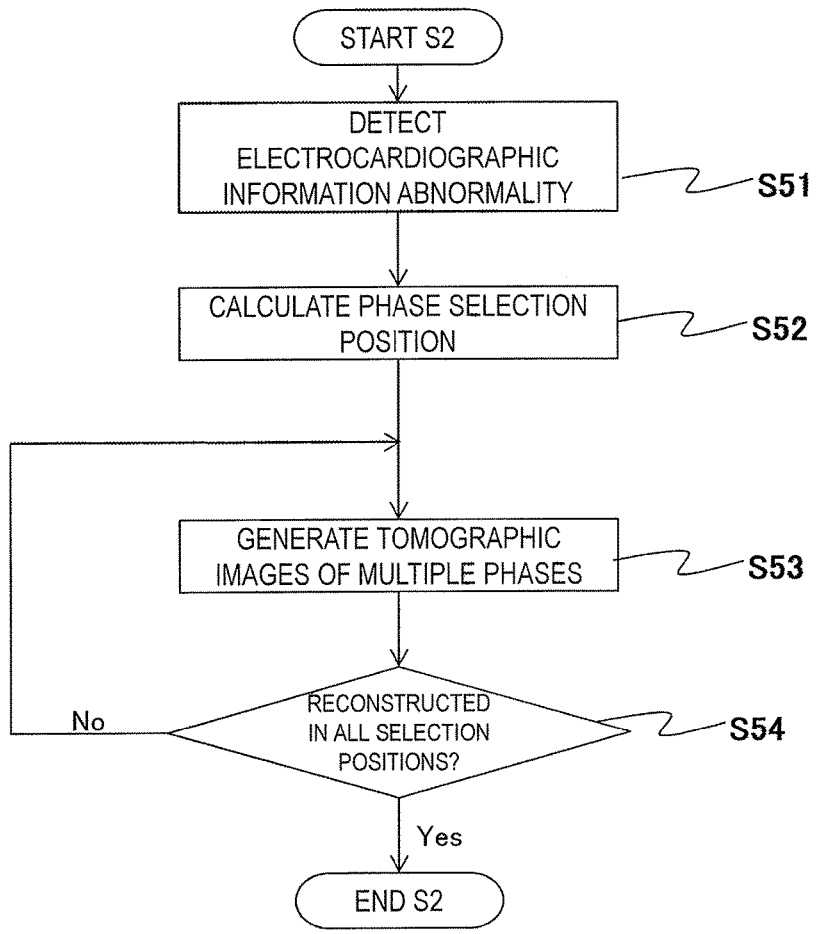
FIG. 17 is a flow chart illustrating a procedure of the selection image generation process (Step S2 of FIG. 3) in a case of setting the phase selection positions as the body-axis direction positions scanned at a time when movement information has an abnormality.

FIG. 17 illustrates a process flow of using abnormality occurrence positions of movement information as references to determine phase selection potions.

The image processing device 403 detects an abnormal state from acquired electrocardiographic information (Step S51). There are various methods for detecting the abnormal state. For example, error output from the electrocardiograph 7 may be used, and time that is not within the normal value range in which an R-wave interval time (one pulse time) was predetermined may be determined as the abnormal state.

The image processing device 403 calculates phase selection potions based on time when the abnormal state of electrocardiographic information detected in Step S51 occurred (Step S52). For example, in the illustrated electrocardiographic waveform of FIG. 16, a phase selection position p1 is a scanning position corresponding to time when noise is mixed in the electrocardiographic information. Also, a phase selection position p2 is a scanning position corresponding to time when arrhythmia occurred.

After determining the phase selection positions p1 and p2, the image processing device 403 generates tomographic images of a plurality of phases (the selection images 80) respectively in the determined phase selection positions p1 and p2 (Step S53). Until the selection images 80 are reconstructed in all the phase selection positions, the Step S53 process (tomographic image generation) will be repeatedly executed (Step S54: No→Step S53). When the selection images 80 are reconstructed in all the phase selection positions (Step S54: Yes), the procedure shifts to Step S3 of FIG. 3.

As described above, the image processing device 403 sets positions where abnormalities occurred in movement information as phase selection positions. Hence, an operator can pay much attention in the phase selection positions where abnormalities occurred in movement information to select a movement phase suitable for diagnosis.

Fifth Embodiment

Next, a fifth embodiment of the present invention will be described. Although an example of setting scanning positions where abnormalities occurred in movement information as phase selection positions is described in the fourth embodiment, on the contrary to this, the scanning positions where abnormalities occurred in movement information may be excluded from the phase selection positions.

For example, as described in the first to third embodiments, in a case where scanning positions corresponding to intermediate positions between adjacent R-waves are set as phase selection positions; where scanning positions at which the reference R-waves switch are set as the phase selection positions; or where scanning positions including a diagnostically important site and/or another target site are set as the phase selection positions, scanning positions where electrocardiographic information is abnormal may be excluded from these phase selection positions.

This can limit phase selection positions to scanning positions having no abnormalities in electrocardiographic information, which can reduce the number of the selection images 80 that are generated and the number of operations for selecting a diagnostic phase.

Sixth Embodiment

Next, a sixth embodiment of the present invention will be described. Although tomographic images of cross sections vertical to the body-axis direction are the selection images 80 in the first to fifth embodiments, the present invention is not limited to this. For example, in image diagnosis, used are three-dimensional images such as MPR (Multi-Planar Reconstruction) images and volume rendering images. Therefore, these three-dimensional images may be generated as the selection images 80 instead of the tomographic images of cross sections vertical to the body-axis direction.

Figure 18:
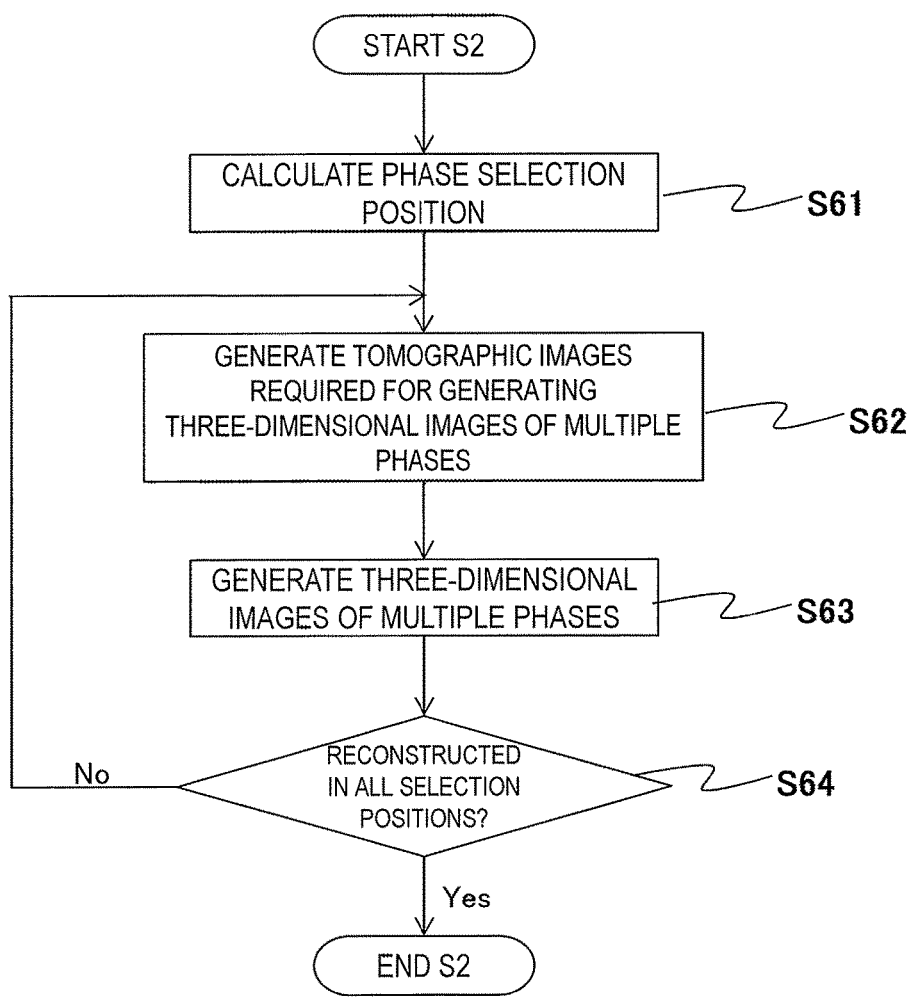
FIG. 18 is a flow chart illustrating a processing procedure of the selection image generation process (Step S2 of FIG. 3) in a case of generating the selection images 80 as three-dimensional images.

FIG. 18 is a process flow in a case of generating three-dimensional images as the selection images 80. The image processing device 403 first calculates phase selection positions p1, p2, . . . using any methods of the first to fifth embodiments (Step S61). Next, tomographic images required to generate the three-dimensional images (for example, MPR images) including the calculated phase selection positions p1, p2, . . . (Step S62). Normally, tomographic images in a plurality of cross-sectional positions are required to generate the three-dimensional images. The number (range) of required tomographic images varies depending on generation conditions of the three-dimensional images (such as angles and rendering conditions of the MPR images).

The image processing device 403 generates three-dimensional images of a plurality of phases from the tomographic images in a plurality of cross sections that were generated in Step S62. (Step S63). The processes S62 and S63 are repeatedly executed in all the phase selection positions evaluated in Step S61 (Step S64: No→Steps S62 and S63). When the three-dimensional images are reconstructed in all the phase selection positions (Step S64: Yes), the procedure shifts to Step S3 of FIG. 3.

As described above, the selection images 80 that are generated in the present invention are not limited to tomographic images of cross sections vertical to the body axis and can be extended to three-dimensional images such as MPR images and volume rendering images.

Seventh Embodiment

Next, a seventh embodiment of the present invention will be described.

As described in the first embodiment, the movement phase distribution 90 that is calculated in Step S5 (phase distribution calculation process) is evaluated by calculating an interpolation (or using another function) based on selected phases respectively for each of phase selection positions. Therefore, there is a possibility that static phases are not represented as the entire diagnostic site. It is desirable that an operator can add a correction to the movement phase distribution 90 using the input device 406 or another user-operated means.

Figure 19:
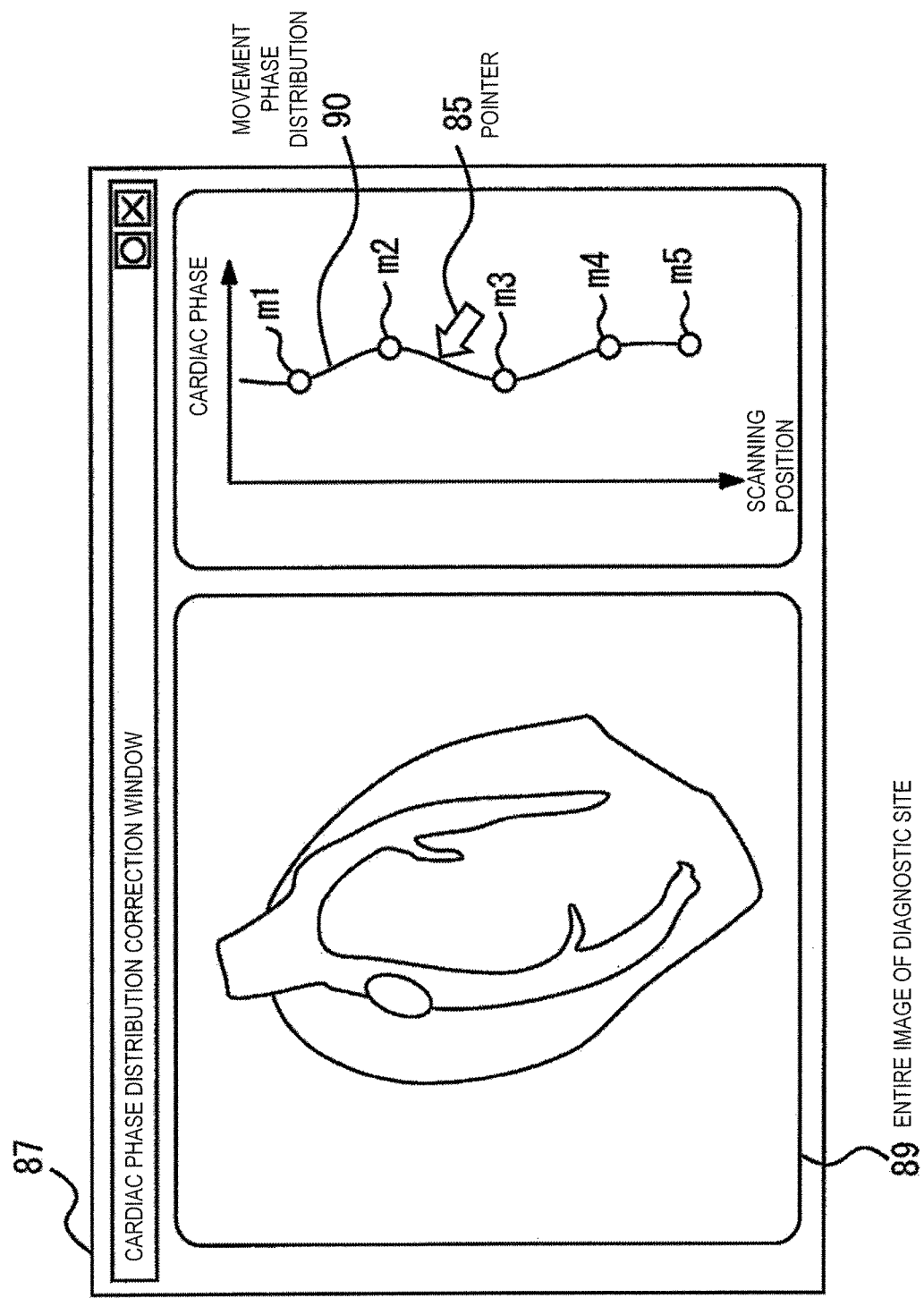
FIG. 19 is an example of a cardiac phase distribution correction window 87 for correcting the calculated movement phase distribution 90.

FIG. 19 illustrates an example of the cardiac phase distribution correction window 87 of the calculated movement phase distribution 90.

On the cardiac phase distribution correction window 87, for example, the entire image 89 of a diagnostic site and the movement phase distribution 90 of the entire diagnostic site are arranged and displayed. The vertical axes of the entire image 89 of the diagnostic site and the movement phase distribution 90 are in the body-axis direction.

As illustrated in FIG. 19, an operator can correct the curve shape of the movement phase distribution 90 by operating the pointer 85 on the window through the input device 406 such as a mouse. Also, it is desirable that the image processing device 403 reconstructs tomographic images in cardiac phases corresponding to the corrected movement phase distribution 90 immediately after correcting the movement phase distribution 90 and updates the entire image 89 of a diagnostic site in real time.

As described above, if an operator can correct a shape of the calculated movement phase distribution 90, images more according to an intention of the operator can be generated. Also, by correcting and displaying diagnostic images in real time according to correction operations of the movement phase distribution 90, the correction results can be checked immediately, which can perform the operations efficiently.

Eighth Embodiment

Next, an eighth embodiment of the present invention will be described.

The movement phase distribution 90 can be calculated without executing the presentation process of the selection images 80 in Step S3 and the diagnostic phase selection process in Step S4 of FIG. 3 in all the phase selection positions. In the eighth embodiment, the X-ray CT apparatus 1 can set selection priority for the phase selection positions in order to generate the selection images in order from a phase selection position with higher priority and select a diagnostic phase.

Figure 20:
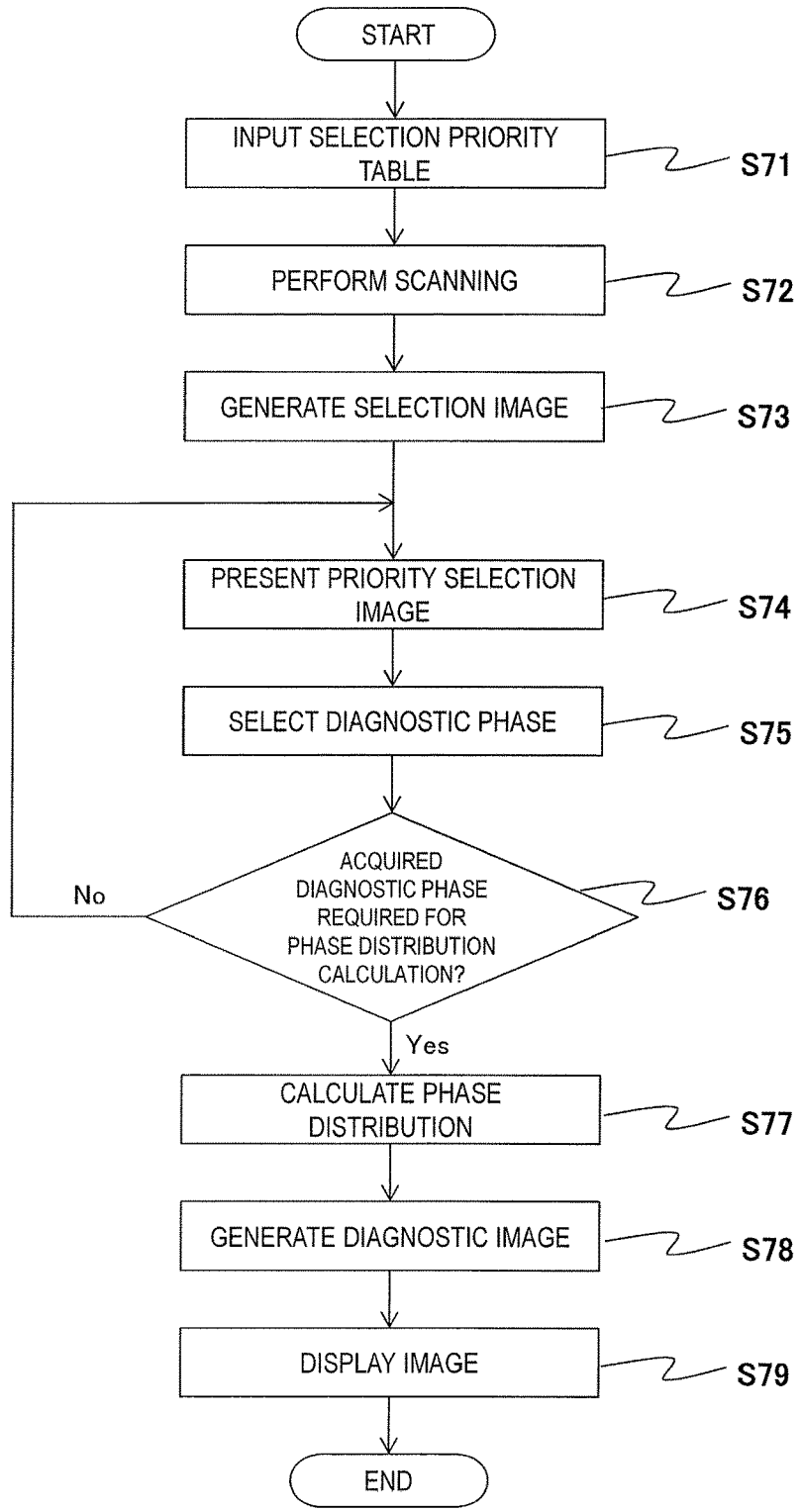
FIG. 20 is a flow chart explaining a process flow in a case of presenting selection images based on selection priority.

FIG. 20 illustrates a flow chart showing the flow of the entire scanning process in a case of generating and presenting the selection images in light of the selection priority.

First, the system controller 401 of the X-ray CT apparatus 1 receives an input of a selection priority table T (Step S71). The selection priority table T is a table that stores priorities of generating and presenting the selection images 80. FIG. 21 is an example of the selection priority table T.

It is desirable that the selection priority can be respectively set for classifications such as site information of the heart, form information such as stenosis and calcification, electrocardiographic waveform information, etc.

In the selection priority table T illustrated in FIG. 21, classifications such as "SITE"; "FORM"; and "ELECTROCARDIOGRAPHIC WAVEFORM" are provided so that the selection priority can be set for each classification. For example, the selection priorities in the respective phase selection positions are set for "SITE" by priority points as follows: "80 (points)" in "PROXIMAL (the upper part of the heart)"; "60 (points)" in "MEDIAN (the central part of the heart)"; and "40 (points)" in "DISTAL (the lower part of the heart)". Also, classifications such as "STENOSIS"; "CALCIFICATION"; and "BRANCHING" are provided for "FORM" so that the selection priority can be set for each classification. In the example of FIG. 21, the high priority, "90 (points)", is set for any of the selection priorities of the sites indicating "STENOSIS"; "CALCIFICATION"; and "BRANCHING". Also, classifications such as "NOISE" and "ARRHYTHMIA" are provided for "ELECTROCARDIOGRAPHIC WAVEFORM", and the selection priorities of "NOISE" and "ARRHYTHMIA" are set to "30 (points)" and "50 (points)" respectively.

When the selection priority table T is input by an operator in Step S71, the system controller 401 stores the selection priority table T in the storage unit.

Next, the system controller 401 starts scanning (Step S72). Electrocardiographic information is also measured together with scanning. The image processing device 403 obtains scan data and movement information acquired by scanning and generates the selection images 80 (Step S73). In order to perform scanning and generating the selection images 80, any methods of the above first to seventh embodiments may be used.

When the selection images 80 are generated in all the phase selection positions in Step S73, the image processing device 403 presents the selection images 80 in order from a selection image 80 with the highest priority according to the contents of the selection priority table T input in Step S71 (Step S74).

Specifically, the selection images 80 in the phase selection positions including "STENOSIS"; "CALCIFICATION"; and "BRANCHING" for which the selection priority was set to "90" are first presented in the example of using the selection priority table T of FIG. 21.

At the step where the operator selects the diagnostic phase from a plurality of the presented selection images 80 (Step S75), whether or not a diagnostic phase required to calculate the movement phase distribution 90 was acquired by an operator is determined (Step S76). When a command to further add a diagnostic phase is input (Step S76: No), the image processing device 403 presents a selection image 80 in a phase selection position of the next highest selection priority (Step S74).

The image processing device 403 presents a selection image 80 in a phase selection position corresponding to "PROXIMAL" for which the selection priority is set to the next highest point "80" and receives a diagnostic phase selected by an operator from a plurality of the presented selection images 80 (Steps S74 and S75). When a command to further add a diagnostic phase is input (Step S76: No), the image processing device 403 presents a selection image 80 in a phase selection position in which the selection priority is the next highest (Step S74).

In a case where an operator determines that adding a diagnostic phase is unnecessary after repeating the processes of Steps S74 to S76 (Step S76: Yes), the image processing device 403 calculates the movement phase distribution 90 using the selection image 80 and the phase selection position as an index in the same manner as the first embodiment (Step S77), generates diagnostic images in the respective body-axis direction positions based on the movement phase distribution 90 (Step S78), and then displays the diagnostic images on the display device 405 (Step S79).

As described above, the X-ray CT apparatus 1 of the eighth embodiment can present the selection images 80 in order from a phase selection position in which the selection priority is higher, select a diagnostic phase, and discontinue the selection halfway by the operator's command at the step where required diagnostic phases are selected.

This can further reduce the operation time of the entire process.

Ninth Embodiment

Next, described will be another example of the phase selection window as a ninth embodiment of the present invention.

Figure 22:
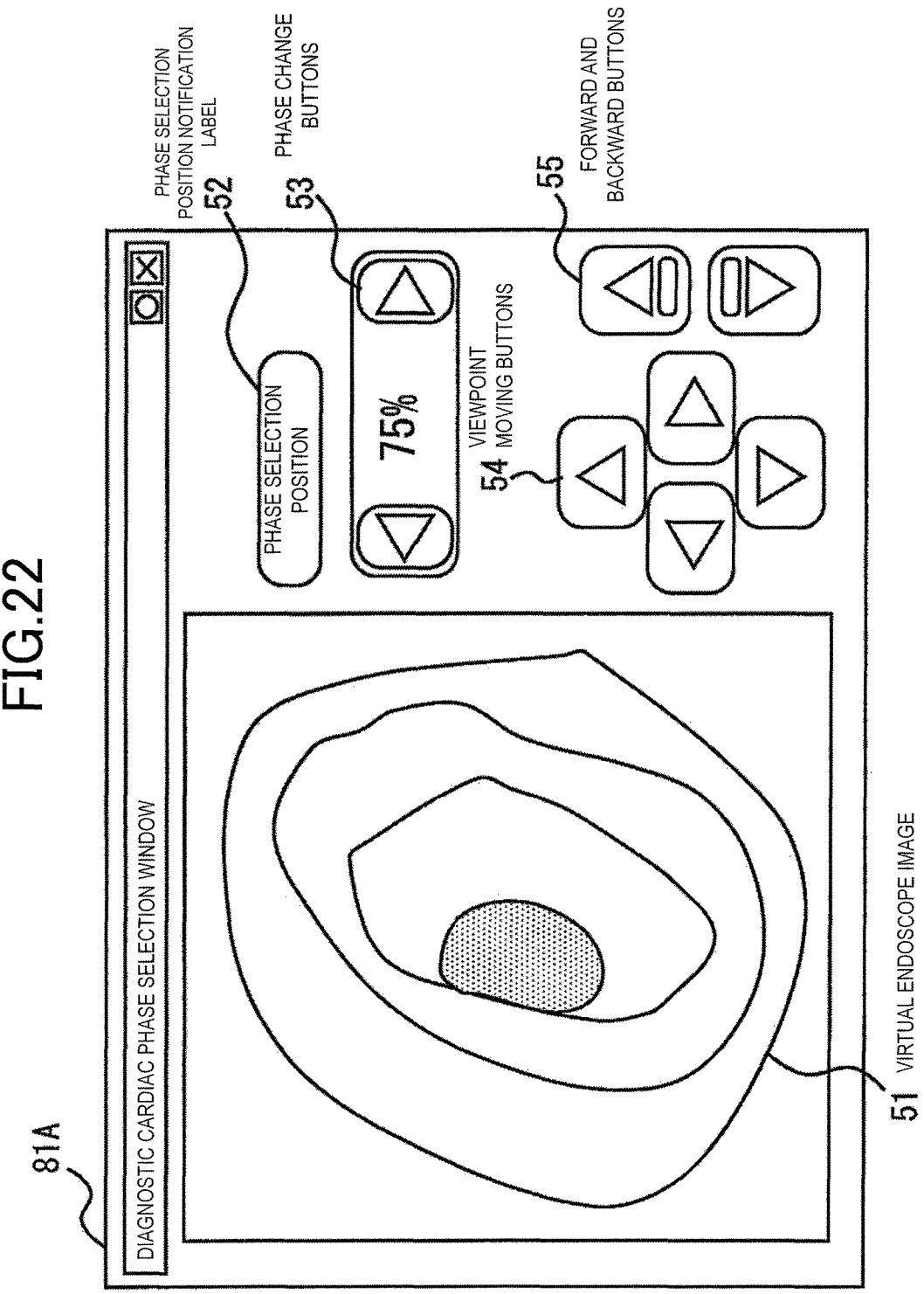
FIG. 22 is an example of a diagnostic cardiac phase selection window 81A for specifying a diagnostic phase after an operator specifies a phase selection position on a virtual endoscope image 51.

FIG. 22 is an example of the diagnostic cardiac phase selection window 81A which can be displayed when a diagnostic phase is selected.

An arbitrary three-dimensional image is presented on the diagnostic cardiac phase selection window 81A illustrated in FIG. 22. In the example of FIG. 22, a virtual endoscope image 51 of the coronary artery is displayed. The virtual endoscope image 51 is a three-dimensional image generated based on a CT image imitating a view from the inside of a luminal organ.

The diagnostic cardiac phase selection window 81A is provided with viewpoint moving buttons 54 and forward and backward buttons 55 as a button group for operating a display state of the virtual endoscope image 51. The phase selection position notification label 52 turns on in a case where a displayed position of the virtual endoscope image 51 includes a phase selection position. Phase change buttons 53 are operated to change a movement phase of the displayed virtual endoscope image 51.

Moving the viewpoint forward and backward in an organ running direction is operated with the forward and backward buttons 55, and changing the viewpoint in the vertical and horizontal directions is operated with the viewpoint moving buttons 54. An operator moves the display of the virtual endoscope image 51 forward and backward in a coronary artery running direction using each of the buttons 54 and 55. When the viewpoint passes by a phase selection position, the system controller 401 makes the phase selection position notification label 52 blink. The operator selects an optimal cardiac phase using the phase change buttons 53 in the phase selection position. The image processing device 403 reconstructs the virtual endoscope image 51 in a phase selected according to the operation of the phase change buttons 53 and updates a display state of the virtual endoscope image 51 in real time. The operator can select an optimal diagnostic phase while checking the virtual endoscope image 51. The similar process is performed for the entire coronary artery.

Thus, in the diagnostic cardiac phase selection window 81A, a cardiac phase can be selected in each phase selection position in conjunction with the operation of the virtual endoscope image. The image processing device 403 calculates the movement phase distribution 90 of the entire diagnostic site based on a movement phase selected in each phase selection position. Also, tomographic images finally used for diagnosis are reconstructed according to the movement phase distribution 90.

Tenth Embodiment

Next, as a tenth embodiment of the present invention, described will be a processing example suitable in a case of performing electrocardiographic synchronous scanning that scans while controlling an X-ray irradiation amount by synchronizing with electrocardiographic information.

Some methods of scanning the heart achieves exposure reduction by synchronizing with electrocardiographic information during scanning and performing X-ray exposure in an arbitrary cardiac phase (hereinafter, referred to as electrocardiographic synchronous scanning).

Figure 23:
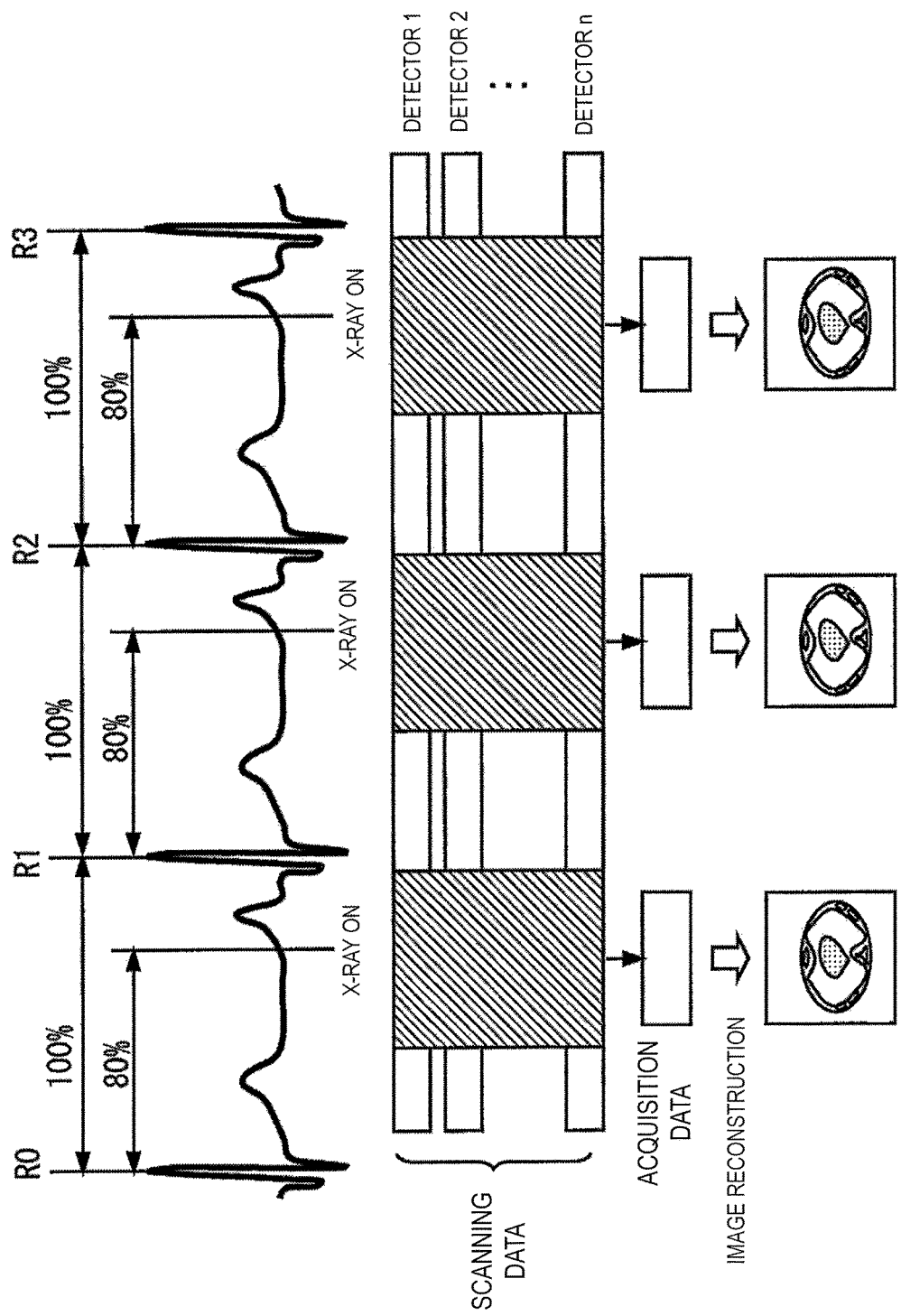
FIG. 23 illustrates scanning for controlling X-ray exposure by synchronizing with movement information.

FIG. 23 is a general example of electrocardiographic synchronous scanning.

In this method, an operator previously sets a cardiac phase before scanning. In the example of FIG. 23, X-ray exposure is controlled so that image reconstruction can be performed in relative 80% positions at adjacent R-wave intervals. In most cases, exposure timing starts using R-waves as references. Scanning is performed at time intervals wider than data widths required for the image reconstruction, and the data ranges are adjusted, which can realize the image reconstruction in different cardiac phases. The present invention can be applied also to such selection of the cardiac phases in electrocardiographic synchronous scanning.

Figure 24:
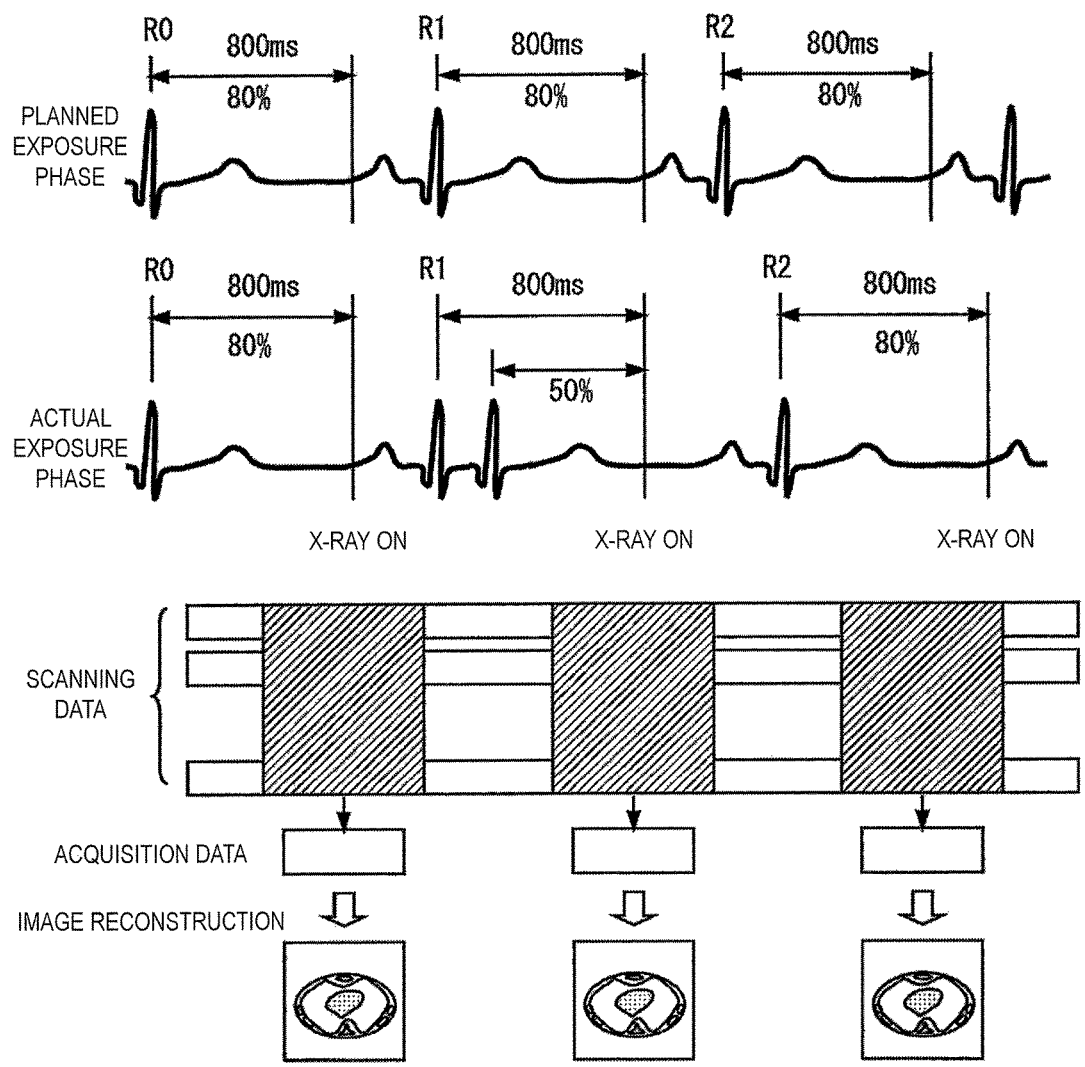
FIG. 24 illustrates differences between estimated movement information and actual movement information.

If unintended pulse variation occurs while the electrocardiographic synchronous scanning is being executed, the problem is that X-ray exposure cannot be performed in previously estimated cardiac phases. FIG. 24 illustrates an example of a case where the pulse variation occurs.

In a case where cardiac phases to be exposed are set to relative 80% positions at adjacent R-wave intervals by estimating a patient whose pulse rate is 60 bpm (one pulse time is 1,000 ms), time after 800 ms from an R-wave is used as a target to determine an X-ray exposure start timing and an exposure time. However, as illustrated in "ACTUAL EXPOSURE PHASE" of FIG. 24, X-ray exposure is performed on the 50% position that is the unintended cardiac phase if unintended pulse movement occurs after R-wave generation in R1. In this case, an operator needs to generate tomographic images of a plurality of cardiac phases and search for a diagnostically optimal cardiac phase.

The X-ray CT apparatus 1 of the present invention may use such a scanning position, in which X-ray exposure could not performed in an intended cardiac phase, as a reference in order to calculate a phase selection position. The image processing device 403 calculates a cardiac phase actually exposed for each R-wave used as an exposure reference and compares the cardiac phase with the planned cardiac phase for the difference value. Then, in a case where the difference value exceeds a preset threshold value, the cardiac phase is set as a phase selection position. Alternatively, the cardiac phase is excluded from phase selection positions.

In the example of FIG. 24, whether or not to set an R-wave in R1 as a phase selection position is determined by comparing 80% that is the planned exposure phase and 50% that is the actual exposure phase.

The tenth embodiment can determine optimal phase selection positions even in a case where pulses are not as expected when scanning is performed by synchronizing with electrocardiographic information.

Eleventh Embodiment

Next, an example of another diagnostic cardiac phase selection window 81B will be described as an eleventh embodiment of the present invention.

In the diagnostic cardiac phase selection window 81B of FIG. 25, the selection images 80 of the respective phase selection positions p1, p2, and p3 are displayed in a grid pattern. The vertical direction of the window indicates the body-axis direction, and the horizontal direction of a selection image display field indicates movement phases.

In the diagnostic cardiac phase selection window 81B, displayed is an entire image 89 of the diagnostic site together with such a selection image group. The entire image 89 of the diagnostic site is a three-dimensional image (such as a volume rendering image) illustrating the entire diagnostic site, and the body-axis direction positions are in the vertical direction of the window. Lines (guide displays G1, G2, and G3) are superimposed and displayed corresponding to the phase selection positions on the entire image 89 of the diagnostic site. Hence, an operator can intuitively understand the phase selection positions during phase selection operations.

Also, the guide displays G1, G2, and G3 illustrated in FIG. 25 may be used for adjusting and adding phase selection positions. FIG. 26 illustrates the example.

An operator can adjust positions of the guide displays G1, G2, and G3 by using the input device 406 such as a mouse to operate the pointer 85 on the window. Also, it may be configured so that a guide display G4 indicating a new phase selection position can be added by moving the pointer 85 to an arbitrary position on the entire image 89 and performing a special operation such as double-clicking the mouse.

The image processing device 403 sets a scanning position equivalent to a moved or added line position (guide display position) as an adjusted phase selection position, generates the selection images 80 in the adjusted phase selection position, and redraws the selection images 80 in the diagnostic cardiac phase selection window 81B.

As described above, the X-ray CT apparatus 1 of the eleventh embodiment can display the entire image 89 of the diagnostic site with the selection images 80 as the diagnostic cardiac phase selection window 81B for selecting a diagnostic phase, superimpose and display the guide displays G1 to G3 corresponding to body-axis direction positions of the displayed selection images 80 on the entire image 89 of the diagnostic site, and add a phase selection position on the entire image 89 of the diagnostic site. Hence, a user-friendly user interface can be provided.

Although the respective embodiments of the X-ray CT apparatus and the image reconstruction method related to the present invention are described above, the present invention is not limited to the above embodiments. It is apparent that a person skilled in the art could arrive at various modified examples or amended examples within the scope of the technical ideas disclosed in the present invention, and it is understood that these naturally belong to the technical scope of the present invention.

REFERENCE SIGNS LIST

1: X-ray CT apparatus
2: scanner gantry
3: bed table
201: X-ray tube
202: scanner controller
205: X-ray detector
210: rotating disk drive unit
4: operation console
401: system controller
403: image processing device
405: display device
406: input device
41: selection image generation unit
42: selection image presentation unit
43: phase selection unit
44: phase distribution calculating unit
45: diagnostic image generating unit
46: diagnostic site extraction unit
47: selection priority setting unit
6: object
7: electrocardiograph (movement information measuring device)
81: phase selection window
89: entire image of a diagnostic site
p1 and p2: phase selection positions
m1 and m2: diagnostic phases (selected movement phases)
G1 to G4: guide displays

The invention claimed is:

1. An X-ray CT apparatus comprising:
    an X-ray source that generates X-rays;
    an X-ray detector that is placed opposite to the X-ray source and detects X-rays transmitted through an object;
    a data acquisition device that acquires scan data corresponding to the transmission X-rays detected by the X-ray detector;
    a movement information measuring device that measures movement information of a diagnostic site in or on the object;
    a selection image generation unit that obtains the scan data and the movement information of the diagnostic site during scanning, determines phase selection positions based on the obtained scan data or the movement information, and generates, based on the scan data and for each of the phase selection positions, plural selection images corresponding to a plurality of respective movement phases;
    a presentation unit that presents the selection images generated by the selection image generation unit;
    a phase selection unit that receives, for each of the phase selection positions, selection of an arbitrary movement phase associated with a corresponding selection image selected by an operator from the selection images, presented by the presentation unit and corresponding to the respective movement phases;
    a calculating unit that calculates, based on the selected movement phase for said each of the phase selection positions which correspond to respective body-axis direction positions, a movement phase distribution which shows an optimal movement phase of the entire diagnostic site; and
    a diagnostic image generating unit that determines, based on the movement phase distribution and for reconstructing diagnostic images corresponding to the respective body-axis direction positions, diagnostic phases corresponding to the respective diagnostic images to be reconstructed, and reconstructs the diagnostic images corresponding to the diagnostic phases.

2. The X-ray CT apparatus according to claim 1, wherein the phase selection positions are provided using a period of the movement information as a reference.

3. The X-ray CT apparatus according to claim 1, further comprising:
    an extraction unit that generates evaluation images of the diagnostic site based on the scan data and extracts a site presenting anatomical features or at least a portion of the diagnostic site, from the evaluation images,
    wherein the selection image generation unit determines, based on the site extracted by the extraction unit, the phase selection positions which correspond to the respective body-axis direction positions of the diagnostic images to be generated by the diagnostic image generating unit.

4. The X-ray CT apparatus according to claim 1, wherein the phase selection positions are set as the body-axis direction positions scanned at a time when the movement information has an abnormality.

5. The X-ray CT apparatus according to claim 1, wherein the phase selection positions are set as the body-axis direction positions excluding scanning positions at a time when the movement information has an abnormality.

6. The X-ray CT apparatus according to claim 1, wherein the calculating unit sets the movement phase distribution as a curve or a straight line to be evaluated based on a relationship between the phase selection positions and the movement phases selected in each phase selection position.

7. The X-ray CT apparatus according to claim 1, wherein each of the movement phases is represented by a percentage of an interval between R-waves, and the calculating unit sets the movement phase distribution as an average value of movement phases selected in a plurality of the phase selection positions.

8. The X-ray CT apparatus according to claim 1, wherein the calculating unit further receives correction of the calculated movement phase distribution.

9. The X-ray CT apparatus according to claim 1, further comprising:
   a selection priority setting unit that sets and stores, for each phase selection position amongst the phase selection positions, a selection priority associated with the phase selection position,
   wherein the presentation unit presents the selection images of the plurality of movement phases in priority order in which each selection image corresponding to a phase selection position associated with a selection priority that is higher than those of remaining selection images is presented prior to said remaining selection images.

10. The X-ray CT apparatus according to claim 1, further comprising:
    a controller that controls X-ray exposure based on movement information during scanning,
    wherein the selection image generation unit evaluates differences between planned movement phases which were previously planned before scanning and actually exposed movement phases and determines the phase selection positions using the evaluated differences as references.

11. The X-ray CT apparatus according to claim 1, wherein the presentation unit displays an entire image illustrating an entire diagnostic site with the selection images and provides guide displays on the entire image corresponding to body-axis direction positions of the selection images.

12. The X-ray CT apparatus according to claim 11, further comprising:
    a phase selection position addition unit that adds an additional phase selection position,
    wherein the selection image generation unit further generates selection images of a plurality of movement phases for the additional phase selection position.

13. An image reconstruction method performed by an image processing device, the method including the steps of:
    (a) obtaining scan data that were measured by an X-ray CT apparatus and movement information of a diagnostic site during scanning, determining phase selection positions based on the obtained scan data or the acquired movement information, and generating, based on the scan data and for each of the phase selection positions, plural selection images corresponding to a plurality of respective movement phases;
    (b) presenting the selection images generated by (a);
    (c) determining, for each of the phase selection positions, an arbitrary movement phase associated with a corresponding selection image selected by an operator from the selection images, presented by (b) and corresponding to the respective movement phases;
    (d) calculating, based on the arbitrary movement phase for said each of the phase selection positions which correspond to respective body-axis direction positions, a movement phase distribution which shows an optimal movement phase of the entire diagnostic site; and
    (e) determining, based on the movement phase distribution and for reconstructing diagnostic images corresponding to the respective body-axis direction positions, diagnostic phases corresponding to the respective diagnostic images to be reconstructed, and reconstructing the diagnostic images corresponding to the diagnostic phases.

* * * * *